US005972643A

United States Patent [19]
Lobanenkov et al.

[11] Patent Number: 5,972,643
[45] Date of Patent: Oct. 26, 1999

[54] ISOLATED POLYNUCLEOTIDE MOLECULES ENCODING CTCF, A CCCTC-BINDING FACTOR

[75] Inventors: Victor L. Lobanenkov; Paul E. Neiman, both of Seattle, Wash.; Elena M. Klenova, London; Graham H. Goodwin, Twickenham, both of United Kingdom; Galina N. Filippova; Steven J. Collins, both of Seattle, Wash.; Robert H. Nicolas, Morden, United Kingdom

[73] Assignees: Fred Hutchinson Cancer Research Center, Seattle, Wash.; Cancer Research Campaign Technology, Ltd., London, United Kingdom

[21] Appl. No.: 08/475,844

[22] Filed: Jun. 7, 1995

Related U.S. Application Data

[63] Continuation-in-part of application No. 08/261,680, Jun. 17, 1994, abandoned.

[51] Int. Cl.$^6$ .............................. C12P 21/02; C12N 1/00; C12N 1/21; C12N 5/10
[52] U.S. Cl. .................. 435/69.1; 435/243; 435/252.33; 435/320.1; 435/325; 536/23.5
[58] Field of Search .............................. 536/23.5, 24.31; 435/320.1, 325, 420, 455, 468, 69.1, 471

[56] References Cited

U.S. PATENT DOCUMENTS

| | | | |
|---|---|---|---|
| 5,143,843 | 9/1992 | Mattes et al. | 530/388.85 |
| 5,272,057 | 12/1993 | Smulson et al. | 435/6 |

OTHER PUBLICATIONS

Ngo et al, The Protein Folding Problem and Tertiary Structure Prediction, 1994, Mertz et al (ed.), Birkhauser, Boston, MA, pp. 433 and 492–495.

Fried et al., "Equilibria and Kinetics of Lac Repressor–Operator Interactions by Polyacrylamide Gel Electrophoresis", *Nuc. Acids Res.* 9:6505–6525 (1981).

Beug et al., "Erythroblast Cell Lines Transformed by a Temperature–Sensitive Mutant of Avian Erythroblastosis Virus: A Model System to Study Erythroid Differentiation in Vitro," *J. Cell. Physiol. Suppl.* 1:195–207 (1982).

Shih et al., "Nucleotide Sequence 5' of the Check c–myc Coding Region: Localization of a Noncoding Exon that is Absent from myc Transcripts in Most Avian Leukosis Virus-Induced Lymphomas," *Proc. Natl. Acad. Sci. USA* 81:4697–4701 (1984).

Jacobs et al., "Isolation and Characterization of Genomic and cDNA Clones of Human Erythropoietin", *Nature* 313:806–810 (Feb., 1985).

Lathe, "Synthetic Oligonucleotide Probes Deduced from Amino Acid Sequence Data", *J. Mol. Biol.* 183:1–12 (1985).

Sen et al., "Multiple Nuclear Factors Interact with the Immunoglobulin Enhancer Sequences", *Cell* 46:705–716 (1986).

Bird et al., "CpG–rich Islands and the Function of DNA Methylation," *Nature* 321:209–213 (1986).

Lobanenkov et al., "Sequence–specific DNA–binding Proteins which Interact with (G+C)–rich Sequences Flanking the Chicken c–myc Gene", *Eur. J. Biochem.* 159:181–188 (1986).

Matsudaira, "Sequence from Picomole Quantities of Proteins Electroblotted onto Polyvinylidene Difluoride Membranes", *J. Biol. Chem.* 262:10035–10038 (Jul., 1987).

Kadonaga et al., "Distinct Regions of Sp1 Modulate DNA Binding and Transcriptional Activation," *Science* 242:1566–1570 (1988).

Gould et al., "Use of the DNA Polymerase Chain Reaction for Homology Probing Isolation of Particle cDNA or Genomic Clones Encoding the Iron–sulfur Protein of Succinate Dehydrogenase from Several Species", *Proc. Natl. Acad. Sci. USA* 86:1934–1938 (Mar., 1989).

Sambrook et al., "Molecular Cloning: A Laboratory Manual", Cold Spring Harbor Laboratory Press, Cold Spring Harbor, NY pp. 8.2–8.86, 11.2–11.6 and 13.2–13.104 (1989).

Lobanenkov et al., "CCCTC–Binding Factore (CTCF): A Novel Sequence–specific DNA Binding Protein Which Interacts with the 5'–Flanking Sequence of the Chicken c–myc Gene", *Gene Reg. and AIDS,* Portfolio Publishing Corp., Tx, 45–68 (1989).

Ben–David et al., "Identification and Mapping of a Common Proviral Integration Site Fli–1 in Erythroleukemia Cells Induced by Friend Murine Leukemia Virus", *Proc. Natl. Acad. Sci. USA* 87:1332–1336 (Feb., 1990).

Kim et al., "Ongoing Diversification of the Rearranged Immunoglobulin Light–Chain Gene in a Bursal Lymphoma cell Line," *Mol. Cell. Biol.* 10:3224–3231 (Jun., 1990).

Tsuda et al., "Allele Loss on Chromosome 16 Associated with Progression of Human Hepatocellular Carcinoma", *Proc. Natl. Acad. Sci. USA* 87:6791–6794 (Sep., 1990).

Carter et al., "Allelic Loss of Chromosome 16q and 10q in Human Prostate Camcer", *Proc. Natl. Acad. Sci. USA* 87:8751–8755 (Nov., 1990).

Berg, "Zinc Fingers and Other Metal Binding Domains", *J. Biol. Chem.,* 265:6513–6516 (1990).

Lobanenkov et al., "A Novel Sequence–specific DNA Binding Protein which Interacts with Three Regularly Spaced Direct Repeats of the CCTC–motif in the 5'–flanking Sequence of the Chicken c–myc Gene", *Oncogene* 5:1743–1753 (1990).

van Lohuizen et al., "Tumorigenesis by Slow–transforming Retroviruses—an Update", *Biochimica et Biophysica Acta.* 1032:213–235 (1990).

Blackwood et al., "Max: A Helix–Loop–Helix Zipper Protein that Forms a Sequence–Specific DNA–Binding Complex with Myc," *Science* 251:1211–1217 (Mar., 1991).

(List continued on next page.)

*Primary Examiner*—Terry McKelvey
*Attorney, Agent, or Firm*—Townsend and Townsend and Crew LLP

[57] ABSTRACT

Polynucleotide molecules encoding CTCF are isolated and purified and sequenced. The CTCF proteins and antibodies thereto can be used to identify mutant CTCFs in methods of diagnosis.

16 Claims, No Drawings

OTHER PUBLICATIONS

Ray et al., "Cloning and Characterization of a Human c–myc Promoter–Binding Protein", *Mol. Cell. Biol.* 11:2154–2161 (Apr., 1991).

Ben–David et al., "Friend Virus–Induced Erythroleukemia and the Multistage Nature of Cancer", *Cell* 66:831–834 (1991).

Roy et al., "Cooperative Interaction of an Initiator–Binding Transcription Initiation Factor and the Helix–Loop–Helix Activator USF", *Nature* 354:245–248 (Nov., 1991).

Spencer and Groudine, "Control of c–myc Regulation in Normal and Neoplastic Cells," *Adv. Cancer REs.* 56:1–48 (1991).

Askew et al., "Constitutive c–myc Expression in an IL–3–Dependent Cell Line Suppresses Cell Cycle Arrest and Accelerates Apotosis", *Oncogene* 6:1915–1922 (1991).

El–Baradi and Tomas, "Zinc Finger Proteins: What We Know and What We Would Like To Know," *Mech. Devel.* 35:155–169 (1991).

Kadonaga, "Purification of Sequence–Specific Binding Proteins by DNA Affinity Chromatography," *Methods Enzymol.* 208:10–23 (1991).

Kolluri and Kinniburgh, "Full Length cDNA Sequence Encoding a Nuclease–Sensitive Element DNA Binding Protein," *Nucl. Acids Res.* 17:4771 (1991).

Neiman et al., "Induction of Apoptosis During Normal and Neoplastic B–cell Development in the Bursa of Fabricius," *Proc. Nal. Acad. Sci. USA* 88:5857–5861 (1991).

Tevosian et al., "Regulatory Protein Factor CTCF Interacts with a Segment of the Chicken c–myc Oncogene Promoter, Capable of Changing to a Noncanonical Conformation," *Molecul. Biol. (Moscow)* (Abst) 25:1013–1023 (1991).

Flanagan et al., "Cloning of a Negative Transcription Factor that Binds to the Upstream Conserved Region of Moloney Muring Leukemia Virus," *Mol. Cell. Biol.* 12:38–44 (Jan., 1992).

Morishita et al., "Activation of EVI1 Gene Expression in Human Acute Myelogenous Leukemias by Translocations Spanning 300–400 kilobases on Chromosome Band 3q26", *Proc. Natl. Acad. Sci. USA* 89:3937–3941 (May, 1992).

Bickmore et al., "Modulation of DNA Binding Specificity by Alternative Splicing of the Wilms Tumor wt1 Gene Transcript," *Science* 257:235–237 (Jul., 1992).

Hsu et al., "Multiple Zinc Finger Forms Resulting from Developmentally Regulated Alternative Splicing of a Transcription Factor Gene," *Science* 257:1946–1950 (1992).

Kretzner et al., "Myc and Max Proteins Possess Distinct Transcriptional Activities," *Nature* 359:426–429 (1992).

Kingsley and Winoto, "Cloning of GT Box–Binding Proteins: A Novel Sp1 Multigene Family Regulating T–Cell Receptor Gene Expression," *Mol. Cell. Biol.* 12:4251–4261 (1992).

Pyrc et al., "Isolation of a Novel cDNA Encoding a Zinc–Finger Protein that Binds to Two Sites Within the c–myc Promoter," *Biochem.* 31:4102–4110 (1992).

Bossone et al., "MAZ, a Zinc Finger Protein, Binds to c–MYC and C2 Gene Sequences Regulating Transcriptional Initiation and Termination," *Proc. Natl. Acad. Sci. USA,* 89:7452–7456 (1992).

Krumm et al., "The Block to Transcriptional Elongation within the Human c–myc Gene is Determined in the Promoter–Proximal Region," *Genes 7 Devel.* 6:2201–2213 (1992).

Stappert et al., "A PCR Method for Introducing Mutations into Cloned DNA by Joining an Internal Primer to a Tagged Flanking Primer," *Nucl. Acids Res.* 20:624 (1992).

Stobl and Eick, "Hold Bank of RNA Polymerase II at the Transcription Start Site Mediates Down–Regulation of c–myc in vivo," *EMBO J.* 11:3307–3314 (1992).

Helin et al., "A cDNA Encoding a pRB–Binding Protein with Properties of the Transcription Factor E2F," *Cell* 70:337–350 (1992).

Marcu et al., "myc Function and Regulation," *Annual Rev. Biochem.* 61:809–860 (1992).

St–Arnaud & Moir, "Wnt–1–Inducing Factor–1: a Novel G/C Box–Binding Transcription Factor Regulating the Expression of Wnt–1 during Neuroectodermal Differentiation", *Mol. Cell. Biol.* 13:1590–1598 (Mar., 1993).

Riggs et al., "Yin–Yang 1 Activates the c–myc Promoter", *Mol. Cell. Biol.* 13:7487–7495 (Dec., 1993).

Klenova et al., "CTCF, a Conserved Nuclear Factor Required for Optimal Transcriptional Activity of the Chicken c–myc Gene, is an 11–Zn–Finger Protein Differentially Expressed in Multiple Forms", *Mol. Cell. Biol.* 13:7612–7624 (1993).

Basu et al., "Identification of a Transcriptional Initiator Element in the Cytochrome c Oxidase Subunit Vb Promoter which Binds to Transcription Factors NF–E1 (YY–1,d) and Sp1.", *J. Biol. Chem.* 268:4188–4196 (1993).

Nicolas and Goodwin, "Purification and Cloning of Trascription Factors", Latchman, ed., *Transcription Factors: a Practical Approach,* IRL Press, Oxford, pp. 81–104 (1993).

Kohlhuber et al., "Early Down–Regulation of c–myc in Dimethylsulfoxide–Induced Mouse Erythroleukemia (MEL) Cells is Mediated at the $P_1/P_2$ Promoters," *Oncogene* 8:1099–1102 (1993).

Franklin et al., "BZP, a Novel Serum–Responsive Zinc Finger Protein that Inhibits Gene Transcription", *Mol. Cell. Biol.* 14:6773–6788 (Oct., 1994).

Cole, "The myc Oncogene: Its Role in Transformation and Differentiation", *Annu. Rev. Genet.* 20:361–384 (1986).

Arnold et al., "DNA bending by the silencer protein NeP1 is modulated by TR and RXR", *Nucleic Acids Research,* 24(14):2640–2647 (1996).

Kohne et al., "A Ubiquitous Transcription Factor Synergizes with v–ERBA in Transcription Silencing", *J. Mol. Biol.* 232:747–755 (1993).

Burcin et al., "Factors influencing nuclear receptors in transcriptional repression", *Cancer Biology,* 5:337–345 (1994).

27;

SEQUENCE LISTING (1) GENERAL INFORMATION:

(iii) NUMBER OF SEQUENCES: 21

(2) INFORMATION FOR SEQ ID NO:1:

(i) SEQUENCE CHARACTERISTICS:
      (A) LENGTH: 60 base pairs
      (B) TYPE: nucleic acid
      (C) STRANDEDNESS: double
      (D) TOPOLOGY: linear (ii) MOLECULE TYPE: DNA (genomic)

(vi) ORIGINAL SOURCE:
      (A) ORGANISM: Gallus domesticus (xi) SEQUENCE DESCRIPTION: SEQ ID NO:1:

```
TACTCGGGGG GGGGCACGGA GCCCCTCGGC CGCCCCCTCG CGGCGCGCCC TCCCCGCTCA        60
```

(2) INFORMATION FOR SEQ ID NO:2:

(i) SEQUENCE CHARACTERISTICS:
        (A) LENGTH: 88 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:2:

```
ATTCGAGCTC GCCCGGGGAT CCTCTAGAGC CCCTCGGCCG CCCCCTCGCG GCGCGCCCTC        60

CCCGCTTCTA GAGTCGACCT GCAGCCCA                                          88
```

(2) INFORMATION FOR SEQ ID NO:3:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Gallus domesticus (xi) SEQUENCE DESCRIPTION: SEQ ID NO:3:

```
Met Gly Gly Glu Ala Val Glu Ala Ile Val Glu Glu
1               5                   10
```

(2) INFORMATION FOR SEQ ID NO:4:

(i) SEQUENCE CHARACTERISTICS:
        (A) LENGTH: 4252 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Gallus domesticus (ix) FEATURE:
        (A) NAME/KEY: CDS
        (B) LOCATION: 679..2865

(xi) SEQUENCE DESCRIPTION: SEQ ID NO:4:

```
GAATTCAAGG CAGCCCTATC AGCTCCTCAC CCAACTCACA AAACCCAGCG ATCCTTCAGC        60

CTCCCAACCC CTCCTCGGCA CTAACTCCAC CCCGGCCTCA TGCCACACCT TCCCCGTTCC       120

TATAGCTGAG GCGGCTTCCT GCCCCAGCGG ACGCGGAACG GACGCAAAAC TTCGGGCGCT       180

GCGGATAACG CCCCGCTCCC CTCAGGGCCG GGCCCGGGCG GGGCACAGCC TCCCCTCAGC       240

GCGGCGCCGC CCCGCCCTCC CTACCACGTG ACGCACGCAC GCACGCACGC GAAGTGACGC       300

CGCCGCCCCA GCCCGCGTT TGAAGTTGGC GCGCGCCCCG CGCCCCCCT CCCCCGCCCC        360

GCCCTCCCAG CATGCCCCGC GCGCGGCCGC TTCCCCGCGC GCGCCGTCCC CTCCCCCCCT       420

CCCCTCCCCG CTCCTGCCGG CGGTCCGCGG CAGCCGCGCT CGCGCAGGCG CACTCCGCCC       480

CGCCCGCCGC CATTTTGTGT CCGAAGCGAC TGTGGAGCGA TTAAACCGCG AGCTGGTGCT       540
```

-continued

```
GGGCGCTAGC GGCGGCCGCG GCGGGGCGCG AGGGGAGCGG CGGCTTCGCG GGGCCCGGGG        600

CGGCTGCGGG GCGGCGTGCG GCGGGGCCTC GGCGCTGAGA GCGAGCCCGG CGGGCGGCGG        660

GCGCAGCAGG AAGGTGAA ATG GAA GGT GAA GCA GTT GAA GCC ATT GTG GAG          711
                    Met Glu Gly Glu Ala Val Glu Ala Ile Val Glu
                     1               5                      10

GAA TCC GAA ACT TTT ATA AAG GGG AAA GAG CGA AAA ACC TAT CAG AGA          759
Glu Ser Glu Thr Phe Ile Lys Gly Lys Glu Arg Lys Thr Tyr Gln Arg
            15                  20                  25

CGC CGC GAG GGA GGG CAG GAG GAC GAG GCT TGC CAT ATA GCA CCG AAC          807
Arg Arg Glu Gly Gly Gln Glu Asp Glu Ala Cys His Ile Ala Pro Asn
        30                  35                  40

CAG GCA GAC GGA GGG GAG GTG GTG CAG GAT GTC AAC AGC GGT GTC CAG          855
Gln Ala Asp Gly Gly Glu Val Val Gln Asp Val Asn Ser Gly Val Gln
    45                  50                  55

ATG GTG ATG ATG GAG CAC CTG GAT CCA ACT CTG CTT CAA ATG AAG ACT          903
Met Val Met Met Glu His Leu Asp Pro Thr Leu Leu Gln Met Lys Thr
60                  65                  70                  75

GAA GTA ATG GAA GGT GCC GTG CCT CAG GAA ACG GAG GCT ACG GTG GAT          951
Glu Val Met Glu Gly Ala Val Pro Gln Glu Thr Glu Ala Thr Val Asp
                80                  85                  90

GAT ACG CAG ATC ATA ACG CTT CAG GTT GTT AAT ATG GAA GAG CAG CCT          999
Asp Thr Gln Ile Ile Thr Leu Gln Val Val Asn Met Glu Glu Gln Pro
            95                  100                 105

ATA AAC CTT GGT GAG CTT CAG CTG GTC CAA GTA CCC GTT CCA GTG ACT         1047
Ile Asn Leu Gly Glu Leu Gln Leu Val Gln Val Pro Val Pro Val Thr
        110                 115                 120

GTA CCC GTT GCC ACC ACA TCT GTG GAA GAA CTT CAG GGA GCT TAT GAA         1095
Val Pro Val Ala Thr Thr Ser Val Glu Glu Leu Gln Gly Ala Tyr Glu
    125                 130                 135

AAT GAG GTT TCC AAA GGA GGC CTG CAG GAG GGA GAA CCC ATG ATC TGT         1143
Asn Glu Val Ser Lys Gly Gly Leu Gln Glu Gly Glu Pro Met Ile Cys
140                 145                 150                 155

CAC ACC CTG CCT TTA CCA GAA GGC TTC CAG GTC GTG AAG GTG GGT GCT         1191
His Thr Leu Pro Leu Pro Glu Gly Phe Gln Val Val Lys Val Gly Ala
                160                 165                 170

AAC GGT GAG GTG GAG ACA CTG GAA CAA GGG GAA CTT CAG CCA CAA GAA         1239
Asn Gly Glu Val Glu Thr Leu Glu Gln Gly Glu Leu Gln Pro Gln Glu
            175                 180                 185

GAT CCC AAT TGG CAA AAA GAT CCA GAC TAT CAG CCA CCA GCC AAA AAA         1287
Asp Pro Asn Trp Gln Lys Asp Pro Asp Tyr Gln Pro Pro Ala Lys Lys
        190                 195                 200

ACA AAG AAA AAC AAA AAG AGT AAG CTT CGC TAC ACC GAG GAG GGC AAA         1335
Thr Lys Lys Asn Lys Lys Ser Lys Leu Arg Tyr Thr Glu Glu Gly Lys
    205                 210                 215

GAC GTG GAT GTC TCT GTG TAT GAC TTC GAG GAG GAG CAG CAG GAG GGT         1383
Asp Val Asp Val Ser Val Tyr Asp Phe Glu Glu Glu Gln Gln Glu Gly
220                 225                 230                 235

TTA TTA TCT GAG GTC AAT GCA GAA AAG GTG GTG GGC AAC ATG AAA CCA         1431
Leu Leu Ser Glu Val Asn Ala Glu Lys Val Val Gly Asn Met Lys Pro
                240                 245                 250

CCT AAA CCA ACA AAA ATT AAA AAG AAA GGT GTA AAG AAG ACA TTC CAG         1479
Pro Lys Pro Thr Lys Ile Lys Lys Lys Gly Val Lys Lys Thr Phe Gln
            255                 260                 265

TGT GAA CTG TGC AGT TAC ACT TGT CCA CGC CGT TCC AAC CTG GAC CGC         1527
Cys Glu Leu Cys Ser Tyr Thr Cys Pro Arg Arg Ser Asn Leu Asp Arg
        270                 275                 280

CAC ATG AAA AGC CAC ACT GAT GAA AGA CCA CAC AAG TGC CAT CTC TGT         1575
His Met Lys Ser His Thr Asp Glu Arg Pro His Lys Cys His Leu Cys
    285                 290                 295
```

```
GGC AGG GCT TTT CGG ACA GTC ACG TTA CTG AGG AAC CAC CTC AAC ACT     1623
Gly Arg Ala Phe Arg Thr Val Thr Leu Leu Arg Asn His Leu Asn Thr
300             305                 310                 315

CAC ACA GGT ACT CGC CCT CAC AAG TGC CCA GAC TGC GAC ATG GCC TTT     1671
His Thr Gly Thr Arg Pro His Lys Cys Pro Asp Cys Asp Met Ala Phe
            320                 325                 330

GTG ACC AGC GGA GAG TTG GTT CGG CAT CGC CGC TAC AAA CAC ACC CAT     1719
Val Thr Ser Gly Glu Leu Val Arg His Arg Arg Tyr Lys His Thr His
        335                 340                 345

GAG AAG CCG TTC AAA TGC TCA ATG TGT GAC TAT GCC AGT GTG GAG GTT     1767
Glu Lys Pro Phe Lys Cys Ser Met Cys Asp Tyr Ala Ser Val Glu Val
    350                 355                 360

AGC AAA TTG AAA CGC CAC ATT CGT TCT CAC ACT GGA GAG CGT CCG TTC     1815
Ser Lys Leu Lys Arg His Ile Arg Ser His Thr Gly Glu Arg Pro Phe
365                 370                 375

CAG TGC AGC TTG TGC AGC TAT GCC AGC AGG GAT ACT TAC AAA CTG AAG     1863
Gln Cys Ser Leu Cys Ser Tyr Ala Ser Arg Asp Thr Tyr Lys Leu Lys
380                 385                 390                 395

AGG CAC ATG AGG ACC CAC TCT GGA GAG AAG CCA TAT GAA TGT TAC ATC     1911
Arg His Met Arg Thr His Ser Gly Glu Lys Pro Tyr Glu Cys Tyr Ile
            400                 405                 410

TGC CAT GCT CGC TTC ACT CAA AGT GGT ACC ATG AAG ATG CAC ATT CTG     1959
Cys His Ala Arg Phe Thr Gln Ser Gly Thr Met Lys Met His Ile Leu
        415                 420                 425

CAG AAG CAC ACG GAG AAC GTG GCC AAA TTT CAC TGT CCT CAC TGT GAT     2007
Gln Lys His Thr Glu Asn Val Ala Lys Phe His Cys Pro His Cys Asp
    430                 435                 440

ACT GTT ATA GCG AGA AAG AGT GAC TTG GGT GTT CAT TTG CGA AAG CAG     2055
Thr Val Ile Ala Arg Lys Ser Asp Leu Gly Val His Leu Arg Lys Gln
445                 450                 455

CAT TCC TAC ATT GAA CAG GGC AAG AAG TGT CGT TAC TGT GAT GCT GTG     2103
His Ser Tyr Ile Glu Gln Gly Lys Lys Cys Arg Tyr Cys Asp Ala Val
460                 465                 470                 475

TTT CAT GAG CGC TAT GCC CTC ATA CAG CAT CAA AAG TCT CAC AAG AAC     2151
Phe His Glu Arg Tyr Ala Leu Ile Gln His Gln Lys Ser His Lys Asn
            480                 485                 490

GAG AAG CGC TTC AAG TGT GAC CAG TGT GAT TAT GCA TGC AGA CAG GAG     2199
Glu Lys Arg Phe Lys Cys Asp Gln Cys Asp Tyr Ala Cys Arg Gln Glu
        495                 500                 505

CGG CAC ATG GTC ATG CAT AAA CGG ACC CAT ACT GGA GAA AAG CCT TAT     2247
Arg His Met Val Met His Lys Arg Thr His Thr Gly Glu Lys Pro Tyr
    510                 515                 520

GCC TGT AGC CAT TGT GAT AAA ACC TTC CGT CAG AAA CAG CTC CTT GAT     2295
Ala Cys Ser His Cys Asp Lys Thr Phe Arg Gln Lys Gln Leu Leu Asp
525                 530                 535

ATG CAC TTC AAA CGA TAC CAC GAT CCC AAC TTC GTT CCT GCT GCC TTT     2343
Met His Phe Lys Arg Tyr His Asp Pro Asn Phe Val Pro Ala Ala Phe
540                 545                 550                 555

GTG TGT TCC AAG TGT GGT AAA ACA TTC ACT CGC AGG AAC ACA ATG GCC     2391
Val Cys Ser Lys Cys Gly Lys Thr Phe Thr Arg Arg Asn Thr Met Ala
            560                 565                 570

AGA CAT GCT GAT AAC TGT TCT GGC CTA GAT GGT GGG GAA GGA GAG AAT     2439
Arg His Ala Asp Asn Cys Ser Gly Leu Asp Gly Gly Glu Gly Glu Asn
        575                 580                 585

GGA GGA GAG ACA AAG AAG GGC AAA CGT GGC CGA AAG AGG AAG ATG CGC     2487
Gly Gly Glu Thr Lys Lys Gly Lys Arg Gly Arg Lys Arg Lys Met Arg
    590                 595                 600

TCT AAG AAA GAA GAT TCC TCC GAT AGT GAG GAA AAT GCT GAA CCA GAT     2535
Ser Lys Lys Glu Asp Ser Ser Asp Ser Glu Glu Asn Ala Glu Pro Asp
605                 610                 615
```

```
TTG GAT GAT AAT GAA GAT GAG GAG GAG ACA GCA GTA GAA ATT GAG GCT    2583
Leu Asp Asp Asn Glu Asp Glu Glu Glu Thr Ala Val Glu Ile Glu Ala
620                 625                 630                 635

GAA CCA GAA GTT AGC GCA GAG GCT CCT GCA CCA CCT CCC AGT AAG AAG    2631
Glu Pro Glu Val Ser Ala Glu Ala Pro Ala Pro Pro Pro Ser Lys Lys
                640                 645                 650

AGG AGA GGA AGA CCA CCA GGC AAA GCT GCC ACC CAA ACC AAA CAA TCC    2679
Arg Arg Gly Arg Pro Pro Gly Lys Ala Ala Thr Gln Thr Lys Gln Ser
            655                 660                 665

CAG CCT GCA GCA ATC ATT CAG GTT GAA GAC CAG AAC ACT GGT GAA ATC    2727
Gln Pro Ala Ala Ile Ile Gln Val Glu Asp Gln Asn Thr Gly Glu Ile
        670                 675                 680

GAA AAC ATT ATA GTA GAA GTA AAG AAA GAA CCT GAT GCA GAA ACA GTA    2775
Glu Asn Ile Ile Val Glu Val Lys Lys Glu Pro Asp Ala Glu Thr Val
    685                 690                 695

GAG GAA GAG GAG GAA GCT CAG CCT GCT GTA GTG GAA GCT CCA AAC GGA    2823
Glu Glu Glu Glu Glu Ala Gln Pro Ala Val Val Glu Ala Pro Asn Gly
700                 705                 710                 715

GAC CTC ACT CCT GAG ATG ATT CTC AGC ATG ATG GAC CGG TGATGGAGGA    2872
Asp Leu Thr Pro Glu Met Ile Leu Ser Met Met Asp Arg
                720                 725

AGACCACGCC GGATGACTGA ACTGGCCTGG GCTGTGTTTA AGCGGCTCAA ATCTATTTTT    2932

CCTTTTACCT TTTTTTCTTG GCTTTGGGAA ATGCATCATT TTAGACCATT TTACCAAACA    2992

TACTGGGAAA TAAAACTTCA AAATGATGTT AGAATGTGAT TTAACTAGAA CTTGCTGTTT    3052

TATGTTAGCA TTACAGGATC ATGGAACATT AGGAAATGCT TCGGAGTCCA TGAGGGTTTC    3112

CCGTGAGGTG CTTGATTAGC TTTGTTCTGA GCTGCATTGT AAACAGGGTC CTCGGACGGC    3172

CAGCTTTACG TGCAACGAGT TTTATGATAC AGAAGTGGAA GCCTTGACTA GAGTATGTGG    3232

TAAACCACTC CGGACTTTGC CCTTCCAGTT CCCAGAGTCC TTGAGCCTCC TTCTCTCAGT    3292

AGTGTTTTTA ACTGTAAATG CAGACTTGGG AGGGTTCTAG ACTTTTTAAA TGTTTTTTGC    3352

TTTCCCCCCA CTGACTAGCT CTGGTTCTCC AAGTCGGCTG CACACGGTAG TTTTGGCATG    3412

CTCCAACTGG TTTCTGTCCT TAATATGCTT TGCTTTCTGC AAAGCATTTC TGTAATGGTC    3472

AAGCTTGTAA ATAACTTTTT TTTTTTTTAC ATTTTAATCT TTTTCCATTA ATTAAGAGGT    3532

ATGCAAAAAT ACAGTTGAAA TAAAGCCCTG GTATTTTAAT TCCTTTCGAA CTAAGCGATA    3592

AAGAGGATCA ATAGTGTAAA TGTTGGGAAA GCTGTTGATA ACTGATCACG TAGAGGAGAA    3652

GTGTACCCAA TGCTATTGCT TGTGGAACAG CAGAGCCCCA CAGGTGGAAG CTGGTTTTGA    3712

AGCACACGAG ACCAGCATTG GAAACGTGTA AGGAACCTTC TTTTTGAGTT ATAACCTCAC    3772

GACTACGTTT TCTTTGCTCT ATCTTGTAGT TGTATTTTGT GTTTTATGAA TCCTTTGTTA    3832

AGACAGAAGT GGTGATTTTT AAGTGGGTCA CTGCAGCCCT CAAAAACCTG GCCAGGAAA    3892

TTTTAATAGG TCAGTAATTA CACAATTTTG GATCTCTAAT AAAGACAAAA GGAATAATGT    3952

GAAATACAAA TGATGCCTGT ATATGAAACT GTCACATGTT AAAATATGTA AGCTTTTTAT    4012

AGAGCCTCAG TCTTGCTGAT TTCAAACAAA TTTTTCTTCT ATGTATTGCT TTTAAGAGAG    4072

CTATCAGTTT AGCTATCAGA CTCTAGGTTG ATGCATTTTT GTACTAGCTG TACTGTGTGA    4132

TATTTTTCAT TATTTTAGGA AGCCAACATG GAAAAAAATA CTGTTATAAA ATATGTAATG    4192

GGGTTTGAAA GCTGGGAAGG AGAATATACT GCTGTACAGC TAATAAATAA TAATGGATTA    4252

(2) INFORMATION FOR SEQ ID NO:5:

(i) SEQUENCE CHARACTERISTICS:
        (A) LENGTH: 728 amino acids
        (B) TYPE: amino acid
```

-continued (D) TOPOLOGY: linear (ii) MOLECULE TYPE: protein (xi) SEQUENCE DESCRIPTION: SEQ ID NO:5:

```
Met Glu Gly Glu Ala Val Glu Ala Ile Val Glu Ser Glu Thr Phe
 1               5                  10                  15

Ile Lys Gly Lys Glu Arg Lys Thr Tyr Gln Arg Arg Glu Gly Gly
                20                  25                  30

Gln Glu Asp Glu Ala Cys His Ile Ala Pro Asn Gln Ala Asp Gly Gly
                35                  40                  45

Glu Val Val Gln Asp Val Asn Ser Gly Val Gln Met Val Met Met Glu
    50                  55                  60

His Leu Asp Pro Thr Leu Leu Gln Met Lys Thr Glu Val Met Glu Gly
 65                  70                  75                  80

Ala Val Pro Gln Glu Thr Glu Ala Thr Val Asp Asp Thr Gln Ile Ile
                85                  90                  95

Thr Leu Gln Val Val Asn Met Glu Glu Gln Pro Ile Asn Leu Gly Glu
                100                 105                 110

Leu Gln Leu Val Gln Val Pro Val Pro Val Thr Val Pro Val Ala Thr
                115                 120                 125

Thr Ser Val Glu Glu Leu Gln Gly Ala Tyr Glu Asn Glu Val Ser Lys
    130                 135                 140

Gly Gly Leu Gln Glu Gly Glu Pro Met Ile Cys His Thr Leu Pro Leu
145                 150                 155                 160

Pro Glu Gly Phe Gln Val Val Lys Val Gly Ala Asn Gly Glu Val Glu
                165                 170                 175

Thr Leu Glu Gln Gly Glu Leu Gln Pro Gln Glu Asp Pro Asn Trp Gln
                180                 185                 190

Lys Asp Pro Asp Tyr Gln Pro Pro Ala Lys Lys Thr Lys Lys Asn Lys
                195                 200                 205

Lys Ser Lys Leu Arg Tyr Thr Glu Glu Gly Lys Asp Val Asp Val Ser
    210                 215                 220

Val Tyr Asp Phe Glu Glu Glu Gln Gln Glu Gly Leu Leu Ser Glu Val
225                 230                 235                 240

Asn Ala Glu Lys Val Val Gly Asn Met Lys Pro Pro Lys Pro Thr Lys
                245                 250                 255

Ile Lys Lys Lys Gly Val Lys Lys Thr Phe Gln Cys Glu Leu Cys Ser
                260                 265                 270

Tyr Thr Cys Pro Arg Arg Ser Asn Leu Asp Arg His Met Lys Ser His
    275                 280                 285

Thr Asp Glu Arg Pro His Lys Cys His Leu Cys Gly Arg Ala Phe Arg
290                 295                 300

Thr Val Thr Leu Leu Arg Asn His Leu Asn Thr His Thr Gly Thr Arg
305                 310                 315                 320

Pro His Lys Cys Pro Asp Cys Asp Met Ala Phe Val Thr Ser Gly Glu
                325                 330                 335

Leu Val Arg His Arg Arg Tyr Lys His Thr His Glu Lys Pro Phe Lys
                340                 345                 350

Cys Ser Met Cys Asp Tyr Ala Ser Val Glu Val Ser Lys Leu Lys Arg
    355                 360                 365

His Ile Arg Ser His Thr Gly Glu Arg Pro Phe Gln Cys Ser Leu Cys
    370                 375                 380

Ser Tyr Ala Ser Arg Asp Thr Tyr Lys Leu Lys Arg His Met Arg Thr
385                 390                 395                 400
```

```
His Ser Gly Glu Lys Pro Tyr Glu Cys Tyr Ile Cys His Ala Arg Phe
                405                 410                 415

Thr Gln Ser Gly Thr Met Lys Met His Ile Leu Gln Lys His Thr Glu
                420                 425                 430

Asn Val Ala Lys Phe His Cys Pro His Cys Asp Thr Val Ile Ala Arg
                435                 440                 445

Lys Ser Asp Leu Gly Val His Leu Arg Lys Gln His Ser Tyr Ile Glu
450                 455                 460

Gln Gly Lys Lys Cys Arg Tyr Cys Asp Ala Val Phe His Glu Arg Tyr
465                 470                 475                 480

Ala Leu Ile Gln His Gln Lys Ser His Lys Asn Glu Lys Arg Phe Lys
                485                 490                 495

Cys Asp Gln Cys Asp Tyr Ala Cys Arg Gln Glu Arg His Met Val Met
                500                 505                 510

His Lys Arg Thr His Thr Gly Glu Lys Pro Tyr Ala Cys Ser His Cys
                515                 520                 525

Asp Lys Thr Phe Arg Gln Lys Gln Leu Leu Asp Met His Phe Lys Arg
530                 535                 540

Tyr His Asp Pro Asn Phe Val Pro Ala Ala Phe Val Cys Ser Lys Cys
545                 550                 555                 560

Gly Lys Thr Phe Thr Arg Arg Asn Thr Met Ala Arg His Ala Asp Asn
                565                 570                 575

Cys Ser Gly Leu Asp Gly Gly Glu Gly Glu Asn Gly Gly Glu Thr Lys
                580                 585                 590

Lys Gly Lys Arg Gly Arg Lys Arg Lys Met Arg Ser Lys Lys Glu Asp
                595                 600                 605

Ser Ser Asp Ser Glu Glu Asn Ala Glu Pro Asp Leu Asp Asp Asn Glu
610                 615                 620

Asp Glu Glu Glu Thr Ala Val Glu Ile Glu Ala Glu Pro Glu Val Ser
625                 630                 635                 640

Ala Glu Ala Pro Ala Pro Pro Ser Lys Lys Arg Arg Gly Arg Pro
                645                 650                 655

Pro Gly Lys Ala Ala Thr Gln Thr Lys Gln Ser Gln Pro Ala Ala Ile
                660                 665                 670

Ile Gln Val Glu Asp Gln Asn Thr Gly Glu Ile Glu Asn Ile Ile Val
                675                 680                 685

Glu Val Lys Lys Glu Pro Asp Ala Glu Thr Val Glu Glu Glu Glu
690                 695                 700

Ala Gln Pro Ala Val Val Glu Ala Pro Asn Gly Asp Leu Thr Pro Glu
705                 710                 715                 720

Met Ile Leu Ser Met Met Asp Arg
                725

(2) INFORMATION FOR SEQ ID NO:6:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Gallus domesticus (xi) SEQUENCE DESCRIPTION: SEQ ID NO:6:
```

```
Glu Gly Glu Ala Val Glu Ala Ile Val Glu Glu Ser
1               5                   10
```

(2) INFORMATION FOR SEQ ID NO:7:

(i) SEQUENCE CHARACTERISTICS:
        (A) LENGTH: 12 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Gallus domesticus (xi) SEQUENCE DESCRIPTION: SEQ ID NO:7:

```
His Ile Ala Pro Asn Gln Ala Asp Gly Gly Glu Val
1               5                   10
```

(2) INFORMATION FOR SEQ ID NO:8:

(i) SEQUENCE CHARACTERISTICS:
        (A) LENGTH: 3810 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: Homo sapiens (vii) IMMEDIATE SOURCE:
        (B) CLONE: human CTCF cDNA (ix) FEATURE:
        (A) NAME/KEY: CDS
        (B) LOCATION: 292..2475

(ix) FEATURE:
        (A) NAME/KEY: exon
        (B) LOCATION: 281..1074
        (D) OTHER INFORMATION: /label= exon2

(ix) FEATURE:
        (A) NAME/KEY: exon
        (B) LOCATION: 1075..1245
        (D) OTHER INFORMATION: /label= exon3

(ix) FEATURE:
        (A) NAME/KEY: exon
        (B) LOCATION: 1246..1379
        (D) OTHER INFORMATION: /label= exon4

(ix) FEATURE:
        (A) NAME/KEY: exon
        (B) LOCATION: 1380..1499
        (D) OTHER INFORMATION: /label= exon5

(ix) FEATURE:
        (A) NAME/KEY: exon
        (B) LOCATION: 1500..1649
        (D) OTHER INFORMATION: /label= exon6

(ix) FEATURE:
        (A) NAME/KEY: exon
        (B) LOCATION: 1650..1810
        (D) OTHER INFORMATION: /label= exon7

(ix) FEATURE:
        (A) NAME/KEY: exon
        (B) LOCATION: 1810..1992
        (D) OTHER INFORMATION: /label= exon8

(xi) SEQUENCE DESCRIPTION: SEQ ID NO:8:

```
TGTGTCTGAG CCTGTGGAGC GATTAAACCG TGCGCGGAGC TGCTTCTTTG GCGGCAGCGG      60

CGGCGGCGGT GGCCGGTGCG GACGCGCGGA GCTCGCCGGA GACGCCGGGT GGCCGGAGCC     120

GTGGAGCGGC GGCGGAGCGG GCGCCGCGGG GGGTGTGGCG CGGAGAATGA TTACGGACCT     180

GAAGCCAAAG AACAAGATGC GCTAGTGGAC AGATTGCTGA CCAGGGGCTT GAGAGCTGGG     240

TTCTATTTTC CCTCCTCAAA CTGACTTTGC AGCCACGGAG AGGCAGGGGA A ATG GAA     297
                                                        Met Glu
                                                          1
```

| | | | | | | | | | | | | | | | | |
|---|---|---|---|---|---|---|---|---|---|---|---|---|---|---|---|---|
| GGT | GAT | GCA | GTC | GAA | GCC | ATT | GTG | GAG | GAG | TCC | GAA | ACT | TTT | ATT | AAA | 345 |
| Gly | Asp | Ala | Val | Glu | Ala | Ile | Val | Glu | Glu | Ser | Glu | Thr | Phe | Ile | Lys | |
| | | 5 | | | | 10 | | | | 15 | | | | | | |

| | | | | | | | | | | | | | | | | |
|---|---|---|---|---|---|---|---|---|---|---|---|---|---|---|---|---|
| GGA | AAG | GAG | AGA | AAG | ACT | TAC | CAG | AGA | CGC | CGG | GAA | GGG | GGC | CAG | GAA | 393 |
| Gly | Lys | Glu | Arg | Lys | Thr | Tyr | Gln | Arg | Arg | Arg | Glu | Gly | Gly | Gln | Glu | |
| | 20 | | | | 25 | | | | 30 | | | | | | | |

| | | | | | | | | | | | | | | | | |
|---|---|---|---|---|---|---|---|---|---|---|---|---|---|---|---|---|
| GAA | GAT | GCC | TGC | CAC | TTA | CCC | CAG | AAC | CAG | ACG | GAT | GGG | GGT | GAG | GTG | 441 |
| Glu | Asp | Ala | Cys | His | Leu | Pro | Gln | Asn | Gln | Thr | Asp | Gly | Gly | Glu | Val | |
| 35 | | | | 40 | | | | 45 | | | | | 50 | | | |

| | | | | | | | | | | | | | | | | |
|---|---|---|---|---|---|---|---|---|---|---|---|---|---|---|---|---|
| GTC | CAG | GAT | GTC | AAC | AGC | AGT | GTA | CAG | ATG | GTG | ATG | ATG | GAA | CAG | CTG | 489 |
| Val | Gln | Asp | Val | Asn | Ser | Ser | Val | Gln | Met | Val | Met | Met | Glu | Gln | Leu | |
| | | | | 55 | | | | | 60 | | | | | 65 | | |

| | | | | | | | | | | | | | | | | |
|---|---|---|---|---|---|---|---|---|---|---|---|---|---|---|---|---|
| GAC | CCC | ACC | CTT | CTT | CAG | ATG | AAG | ACT | GAA | GTA | ATG | GAG | GGC | ACA | GTG | 537 |
| Asp | Pro | Thr | Leu | Leu | Gln | Met | Lys | Thr | Glu | Val | Met | Glu | Gly | Thr | Val | |
| | | | 70 | | | | | 75 | | | | | 80 | | | |

| | | | | | | | | | | | | | | | | |
|---|---|---|---|---|---|---|---|---|---|---|---|---|---|---|---|---|
| GCT | CCA | GAA | GCA | GAG | GCT | GCT | GTG | GAC | GAT | ACC | CAG | ATT | ATA | ACT | TTA | 585 |
| Ala | Pro | Glu | Ala | Glu | Ala | Ala | Val | Asp | Asp | Thr | Gln | Ile | Ile | Thr | Leu | |
| | | | | 85 | | | | | 90 | | | | | 95 | | |

| | | | | | | | | | | | | | | | | |
|---|---|---|---|---|---|---|---|---|---|---|---|---|---|---|---|---|
| CAG | GTT | GTA | AAT | ATG | GAG | GAA | CAG | CCC | ATA | AAC | ATA | GGA | GAA | CTT | CAG | 633 |
| Gln | Val | Val | Asn | Met | Glu | Glu | Gln | Pro | Ile | Asn | Ile | Gly | Glu | Leu | Gln | |
| | | 100 | | | | | 105 | | | | | 110 | | | | |

| | | | | | | | | | | | | | | | | |
|---|---|---|---|---|---|---|---|---|---|---|---|---|---|---|---|---|
| CTT | GTT | CAA | GTA | CCT | GTT | CCT | GTG | ACT | GTA | CCT | GTT | GCT | ACC | ACT | TCA | 681 |
| Leu | Val | Gln | Val | Pro | Val | Pro | Val | Thr | Val | Pro | Val | Ala | Thr | Thr | Ser | |
| 115 | | | | | 120 | | | | | 125 | | | | | 130 | |

| | | | | | | | | | | | | | | | | |
|---|---|---|---|---|---|---|---|---|---|---|---|---|---|---|---|---|
| GTA | GAA | GAA | CTT | CAG | GGG | GCT | TAT | GAA | AAT | GAA | GTG | TCT | AAA | GAG | GGC | 729 |
| Val | Glu | Glu | Leu | Gln | Gly | Ala | Tyr | Glu | Asn | Glu | Val | Ser | Lys | Glu | Gly | |
| | | | | 135 | | | | | 140 | | | | | 145 | | |

| | | | | | | | | | | | | | | | | |
|---|---|---|---|---|---|---|---|---|---|---|---|---|---|---|---|---|
| CTT | GCG | GAA | AGT | GAA | CCC | ATG | ATA | TGC | CAC | ACC | CTA | CCT | TTG | CCT | GAA | 777 |
| Leu | Ala | Glu | Ser | Glu | Pro | Met | Ile | Cys | His | Thr | Leu | Pro | Leu | Pro | Glu | |
| | | | | 150 | | | | | 155 | | | | | 160 | | |

| | | | | | | | | | | | | | | | | |
|---|---|---|---|---|---|---|---|---|---|---|---|---|---|---|---|---|
| GGG | TTT | CAG | GTG | GTT | AAA | GTG | GGG | GCC | AAT | GGA | GAG | GTG | GAG | ACA | CTA | 825 |
| Gly | Phe | Gln | Val | Val | Lys | Val | Gly | Ala | Asn | Gly | Glu | Val | Glu | Thr | Leu | |
| | | 165 | | | | | 170 | | | | | 175 | | | | |

| | | | | | | | | | | | | | | | | |
|---|---|---|---|---|---|---|---|---|---|---|---|---|---|---|---|---|
| GAA | CAA | GGG | GAA | CTT | CCA | CCC | CAG | GAA | GAT | CCT | AGT | TGG | CAA | AAA | GAC | 873 |
| Glu | Gln | Gly | Glu | Leu | Pro | Pro | Gln | Glu | Asp | Pro | Ser | Trp | Gln | Lys | Asp | |
| | 180 | | | | | 185 | | | | | 190 | | | | | |

| | | | | | | | | | | | | | | | | |
|---|---|---|---|---|---|---|---|---|---|---|---|---|---|---|---|---|
| CCA | GAC | TAT | CAG | CCA | CCA | GCC | AAA | AAA | ACA | AAG | AAA | ACC | AAA | AAG | AGC | 921 |
| Pro | Asp | Tyr | Gln | Pro | Pro | Ala | Lys | Lys | Thr | Lys | Lys | Thr | Lys | Lys | Ser | |
| 195 | | | | | 200 | | | | | 205 | | | | | 210 | |

| | | | | | | | | | | | | | | | | |
|---|---|---|---|---|---|---|---|---|---|---|---|---|---|---|---|---|
| AAA | CTG | CGT | TAT | ACA | GAG | GAG | GGC | AAA | GAT | GTA | GAT | GTG | TCT | GTC | TAC | 969 |
| Lys | Leu | Arg | Tyr | Thr | Glu | Glu | Gly | Lys | Asp | Val | Asp | Val | Ser | Val | Tyr | |
| | | | | 215 | | | | | 220 | | | | | 225 | | |

| | | | | | | | | | | | | | | | | |
|---|---|---|---|---|---|---|---|---|---|---|---|---|---|---|---|---|
| GAT | TTT | GAG | GAA | GAA | CAG | CAG | GAG | GGT | CTG | CTA | TCA | GAG | GTT | AAT | GCG | 1017 |
| Asp | Phe | Glu | Glu | Glu | Gln | Gln | Glu | Gly | Leu | Leu | Ser | Glu | Val | Asn | Ala | |
| | | | 230 | | | | | 235 | | | | | 240 | | | |

| | | | | | | | | | | | | | | | | |
|---|---|---|---|---|---|---|---|---|---|---|---|---|---|---|---|---|
| GAG | AAA | GTG | GTT | GGT | AAT | ATG | AAG | CCT | CCA | AAG | CCA | ACA | AAA | ATT | AAA | 1065 |
| Glu | Lys | Val | Val | Gly | Asn | Met | Lys | Pro | Pro | Lys | Pro | Thr | Lys | Ile | Lys | |
| | | 245 | | | | | 250 | | | | | 255 | | | | |

| | | | | | | | | | | | | | | | | |
|---|---|---|---|---|---|---|---|---|---|---|---|---|---|---|---|---|
| AAG | AAA | GGT | GTA | AAG | AAG | ACA | TTC | CAG | TGT | GAG | CTT | TGC | AGT | TAC | ACG | 1113 |
| Lys | Lys | Gly | Val | Lys | Lys | Thr | Phe | Gln | Cys | Glu | Leu | Cys | Ser | Tyr | Thr | |

-continued

```
                260                         265                         270
TGT CCA CGG CGT TCA AAT TTG GAT CGT CAC ATG AAA AGC CAC ACT GAT          1161
Cys Pro Arg Arg Ser Asn Leu Asp Arg His Met Lys Ser His Thr Asp
275                 280                 285                 290

GAG AGA CCA CAC AAG TGC CAT CTC TGT GGC AGG GCA TTC AGA ACA GTC          1209
Glu Arg Pro His Lys Cys His Leu Cys Gly Arg Ala Phe Arg Thr Val
                295                 300                 305

ACC CTC CTG AGG AAT CAC CTT AAC ACA CAC ACA GGT ACT CGT CCT CAC          1257
Thr Leu Leu Arg Asn His Leu Asn Thr His Thr Gly Thr Arg Pro His
            310                 315                 320

AAG TGC CCA GAC TGC GAC ATG GCC TTT GTG ACC AGT GGA GAA TTG GTT          1305
Lys Cys Pro Asp Cys Asp Met Ala Phe Val Thr Ser Gly Glu Leu Val
        325                 330                 335

CGG CAT CGT CGT TAC AAA CAC ACC CAC GAG AAG CCA TTC AAG TGT TCC          1353
Arg His Arg Arg Tyr Lys His Thr His Glu Lys Pro Phe Lys Cys Ser
    340                 345                 350

ATG TGC GAT TAC GCC AGT GTA GAA GTC AGC AAA TTA AAA CGT CAC ATT          1401
Met Cys Asp Tyr Ala Ser Val Glu Val Ser Lys Leu Lys Arg His Ile
355                 360                 365                 370

CGC TCT CAT ACT GGA GAG CGT CCG TTT CAG TGC AGT TTG TGC AGT TAT          1449
Arg Ser His Thr Gly Glu Arg Pro Phe Gln Cys Ser Leu Cys Ser Tyr
                375                 380                 385

GCC AGC AGG GAC ACA TAC AAG CTG AAA AGG CAC ATG AGA ACC CAT TCA          1497
Ala Ser Arg Asp Thr Tyr Lys Leu Lys Arg His Met Arg Thr His Ser
            390                 395                 400

GGG GAA AAG CCT TAT GAA TGT TAT ATT TGT CAT GCT CGG TTT ACC CAA          1545
Gly Glu Lys Pro Tyr Glu Cys Tyr Ile Cys His Ala Arg Phe Thr Gln
        405                 410                 415

AGT GGT ACC ATG AAG ATG CAC ATT TTA CAG AAG CAC ACA GAA AAT GTG          1593
Ser Gly Thr Met Lys Met His Ile Leu Gln Lys His Thr Glu Asn Val
    420                 425                 430

GCC AAA TTT CAC TGT CCC CAC TGT GAC ACA GTC ATA GCC CGA AAA AGT          1641
Ala Lys Phe His Cys Pro His Cys Asp Thr Val Ile Ala Arg Lys Ser
435                 440                 445                 450

GAT TTG GGT GTC CAC TTG CGA AAG CAG CAT TCC TAT ATT GAG CAA GGC          1689
Asp Leu Gly Val His Leu Arg Lys Gln His Ser Tyr Ile Glu Gln Gly
                455                 460                 465

AAG AAA TGC CGT TAC TGT GAT GCT GTG TTT CAT GAG CGC TAT GCC CTC          1737
Lys Lys Cys Arg Tyr Cys Asp Ala Val Phe His Glu Arg Tyr Ala Leu
            470                 475                 480

ATC CAG CAT CAG AAG TCA CAC AAG AAT GAG AAG CGC TTT AAG TGT GAC          1785
Ile Gln His Gln Lys Ser His Lys Asn Glu Lys Arg Phe Lys Cys Asp
        485                 490                 495

CAG TGT GAT TAC GCT TGT AGA CAG GAG AGG CAC ATG ATC ATG CAC AAG          1833
Gln Cys Asp Tyr Ala Cys Arg Gln Glu Arg His Met Ile Met His Lys
    500                 505                 510

CGC ACC CAC ACC GGG GAG AAG CCT TAC GCC TGC AGC CAC TGC GAT AAG          1881
Arg Thr His Thr Gly Glu Lys Pro Tyr Ala Cys Ser His Cys Asp Lys
515                 520                 525                 530

ACC TTC CGC CAG AAG CAG CTT CTC GAC ATG CAC TTC AAG CGC TAT CAC          1929
Thr Phe Arg Gln Lys Gln Leu Leu Asp Met His Phe Lys Arg Tyr His
                535                 540                 545

GAC CCC AAC TTC GTC CCT GCG GCT TTT GTC TGT TCT AAG TGT GGG AAA          1977
Asp Pro Asn Phe Val Pro Ala Ala Phe Val Cys Ser Lys Cys Gly Lys
            550                 555                 560

ACA TTT ACA CGT CGG AAT ACC ATG GCA AGA CAT GCT GAT AAT TGT GCT          2025
Thr Phe Thr Arg Arg Asn Thr Met Ala Arg His Ala Asp Asn Cys Ala
        565                 570                 575

GGC CCA GAT GGC GTA GAG GGG GAA AAT GGA GGA GAA ACG AAG AAG AGT          2073
Gly Pro Asp Gly Val Glu Gly Glu Asn Gly Gly Glu Thr Lys Lys Ser
```

-continued

|  |  |
|---|---|
| 580 585 590 | |
| AAA CGT GGA AGA AAA AGA AAG ATG CGC TCT AAG AAA GAA GAT TCC TCT<br>Lys Arg Gly Arg Lys Arg Lys Met Arg Ser Lys Lys Glu Asp Ser Ser<br>595 600 605 610 | 2121 |
| GAC AGT GAA AAT GCT GAA CCA GAT CTG GAC GAC AAT GAG GAT GAG GAG<br>Asp Ser Glu Asn Ala Glu Pro Asp Leu Asp Asp Asn Glu Asp Glu Glu<br>615 620 625 | 2169 |
| GAG CCT GCC GTA GAA ATT GAA CCT GAG CCA GAG CCT CAG CCT GTG ACC<br>Glu Pro Ala Val Glu Ile Glu Pro Glu Pro Glu Pro Gln Pro Val Thr<br>630 635 640 | 2217 |
| CCA GCC CCA CCA CCC GCC AAG AAG CGG AGA GGA CGA CCC CCT GGC AGA<br>Pro Ala Pro Pro Pro Ala Lys Lys Arg Arg Gly Arg Pro Pro Gly Arg<br>645 650 655 | 2265 |
| ACC AAC CAG CCC AAA CAG AAC CAG CCA ACA GCT ATC ATT CAG GTT GAA<br>Thr Asn Gln Pro Lys Gln Asn Gln Pro Thr Ala Ile Ile Gln Val Glu<br>660 665 670 | 2313 |
| GAC CAG AAT ACA GGT GCA ATT GAG AAC ATT ATA GTT GAA GTA AAA AAA<br>Asp Gln Asn Thr Gly Ala Ile Glu Asn Ile Ile Val Glu Val Lys Lys<br>675 680 685 690 | 2361 |
| GAG CCA GAT GCT GAG CCC GCA GAG GGA GAG GAA GAG GAG GCC CAG CCA<br>Glu Pro Asp Ala Glu Pro Ala Glu Gly Glu Glu Glu Glu Ala Gln Pro<br>695 700 705 | 2409 |
| GCT GCC ACA GAT GCC CCC AAC GGA GAC CTC ACG CCC GAG ATG ATC CTC<br>Ala Ala Thr Asp Ala Pro Asn Gly Asp Leu Thr Pro Glu Met Ile Leu<br>710 715 720 | 2457 |
| AGC ATG ATG GAC CGG TGATGGCGGA GCCTTGTGCG TCGCCAGGAC TTCTCTGGGC<br>Ser Met Met Asp Arg<br>725 | 2512 |
| TGTGTTTAAA CGGCCCGCAT CTTAATTTTT CTCCCTTCTT TCTTTTTTTG GCTTTGGGAA | 2572 |
| AAGCATCATT TTACCAAACA TACCGAGAAC GAAAACTTCA AGGATGATGT TAGAAAAAAA | 2632 |
| TGTGATTTAA CTAGAACTTG CTGTCTGATG TTAGCAAATC ATGGAATGTT CTGAGTCCCT | 2692 |
| GAGGGTTTAC TGTGAAGTGC TGAGGACAGT GTTGACAACT AACTCGTTTT CCTAGATGGA | 2752 |
| AACGGAGACA TTGACCCCTC CCTCCATGTG GTAAACCACT CCAGAATGGC CACCAGGCTT | 2812 |
| CCCAGAGTTC TATGGTCTTC TTCCCAAGAG AGTTTTTAAT TGTAAATGCA TACTTGGGAA | 2872 |
| GGACTTAGAG TTTTAAACTG TTTTTTGCTT TTGCTTTTCC CTGACTCCCT TTGCTTGGAG | 2932 |
| TCAGCTGCAC ACCAGTAGTA TGGCATGCTA CGATCAGGTT CTGTCCTGAA AGCTTTGCCT | 2992 |
| CTTTCTTGGC AAAGTTTCTG GTATGGTCAA GCTTGTAAAT AACTTTTTTT ACATTTTAAT | 3052 |
| CTTTTCCATT AATTAAGAGG TTGAAAAGAA GTGCAGTGTA AGAAAACCCA GCATTTTAAT | 3112 |
| TACTTGCAAA TTAAGTTACC ACAGACTCTG TAGTGTGTAA ATGTTGACAA GGAATTGGAT | 3172 |
| CACAATCATG TAGCAGAATG GCACCCAGAC CACTGCCCAC CAGTGACGGA CATGCACGTG | 3232 |
| GCAGATCATG ATTTCCAGCC CACGGAGCCA GCATTTGAAC CTTGTATAAT TAACTTTCAG | 3292 |
| TTATGATTTC CCATCGACAT TTTCTTTGCC CTGTTTGTAG CTGATTGTTG TGTTTTATAA | 3352 |
| ATCTTCTGTT AAGGCAGAAG GGTGATTATG AGTGGTTCAC AGCAGCCCTT ATAAGCTGGG | 3412 |
| CCAGAAAATT TCACTAGGTC AGTAATTTAA ACCTTGGATC TTCAAAAAAT AAAATAATGT | 3472 |
| GAAGCAAAAC CAACTAAAAA GTGATTCTTG CACATGAACT GTCACATGTT TAAAAATGTG | 3532 |
| TTTTTTAGAG AGCCTCAGTC TTACTGATTT CAAACACTTT TTTCTTCTGT GTATTGCTTT | 3592 |
| TAAGAGAGCC ATCAGTTAGC TATCAGACTC TAGGTTGATG CATTTTGTAC TTAGCTGTAC | 3652 |
| TGTGTGATAT TTTTCATTAT TTTAGGACGC CAACATGAGA CCTGTAATAA AATATGTAAT | 3712 |
| GGGGTTGAAA GCTGGGGAGG AGGATCTACT GCTGTACAGC TAATAAATCA TAACGGATTA | 3772 |

ACAAGTGAAA AAAAAAAAAA AAAAAAAAAA AAAAAAA                                       3810

(2) INFORMATION FOR SEQ ID NO:9:

(i) SEQUENCE CHARACTERISTICS:
        (A) LENGTH: 727 amino acids
        (B) TYPE: amino acid
        (D) TOPOLOGY: linear (ii) MOLECULE TYPE: protein (xi) SEQUENCE DESCRIPTION: SEQ ID NO:9:

```
Met Glu Gly Asp Ala Val Glu Ala Ile Val Glu Ser Glu Thr Phe
  1               5                  10                  15

Ile Lys Gly Lys Glu Arg Lys Thr Tyr Gln Arg Arg Glu Gly Gly
                 20                  25                  30

Gln Glu Glu Asp Ala Cys His Leu Pro Gln Asn Gln Thr Asp Gly Gly
                 35                  40                  45

Glu Val Val Gln Asp Val Asn Ser Ser Val Gln Met Val Met Met Glu
 50                  55                  60

Gln Leu Asp Pro Thr Leu Leu Gln Met Lys Thr Glu Val Met Glu Gly
 65                  70                  75                  80

Thr Val Ala Pro Glu Ala Glu Ala Ala Val Asp Asp Thr Gln Ile Ile
                 85                  90                  95

Thr Leu Gln Val Val Asn Met Glu Glu Gln Pro Ile Asn Ile Gly Glu
                100                 105                 110

Leu Gln Leu Val Gln Val Pro Val Pro Val Thr Val Pro Val Ala Thr
                115                 120                 125

Thr Ser Val Glu Glu Leu Gln Gly Ala Tyr Glu Asn Glu Val Ser Lys
130                 135                 140

Glu Gly Leu Ala Glu Ser Glu Pro Met Ile Cys His Thr Leu Pro Leu
145                 150                 155                 160

Pro Glu Gly Phe Gln Val Val Lys Val Gly Ala Asn Gly Glu Val Glu
                165                 170                 175

Thr Leu Glu Gln Gly Glu Leu Pro Pro Gln Glu Asp Pro Ser Trp Gln
                180                 185                 190

Lys Asp Pro Asp Tyr Gln Pro Pro Ala Lys Lys Thr Lys Lys Thr Lys
                195                 200                 205

Lys Ser Lys Leu Arg Tyr Thr Glu Glu Gly Lys Asp Val Asp Val Ser
210                 215                 220

Val Tyr Asp Phe Glu Glu Glu Gln Gln Glu Gly Leu Leu Ser Glu Val
225                 230                 235                 240

Asn Ala Glu Lys Val Val Gly Asn Met Lys Pro Pro Lys Pro Thr Lys
                245                 250                 255

Ile Lys Lys Lys Gly Val Lys Lys Thr Phe Gln Cys Glu Leu Cys Ser
                260                 265                 270

Tyr Thr Cys Pro Arg Arg Ser Asn Leu Asp Arg His Met Lys Ser His
                275                 280                 285

Thr Asp Glu Arg Pro His Lys Cys His Leu Cys Gly Arg Ala Phe Arg
290                 295                 300

Thr Val Thr Leu Leu Arg Asn His Leu Asn Thr His Thr Gly Thr Arg
305                 310                 315                 320

Pro His Lys Cys Pro Asp Cys Asp Met Ala Phe Val Thr Ser Gly Glu
                325                 330                 335

Leu Val Arg His Arg Arg Tyr Lys His Thr His Glu Lys Pro Phe Lys
                340                 345                 350
```

```
Cys Ser Met Cys Asp Tyr Ala Ser Val Glu Val Ser Lys Leu Lys Arg
        355                 360                 365

His Ile Arg Ser His Thr Gly Glu Arg Pro Phe Gln Cys Ser Leu Cys
        370                 375                 380

Ser Tyr Ala Ser Arg Asp Thr Tyr Lys Leu Lys Arg His Met Arg Thr
385                 390                 395                 400

His Ser Gly Glu Lys Pro Tyr Glu Cys Tyr Ile Cys His Ala Arg Phe
                405                 410                 415

Thr Gln Ser Gly Thr Met Lys Met His Ile Leu Gln Lys His Thr Glu
            420                 425                 430

Asn Val Ala Lys Phe His Cys Pro His Cys Asp Thr Val Ile Ala Arg
                435                 440                 445

Lys Ser Asp Leu Gly Val His Leu Arg Lys Gln His Ser Tyr Ile Glu
450                 455                 460

Gln Gly Lys Lys Cys Arg Tyr Cys Asp Ala Val Phe His Glu Arg Tyr
465                 470                 475                 480

Ala Leu Ile Gln His Gln Lys Ser His Lys Asn Glu Lys Arg Phe Lys
                485                 490                 495

Cys Asp Gln Cys Asp Tyr Ala Cys Arg Gln Glu Arg His Met Ile Met
                500                 505                 510

His Lys Arg Thr His Thr Gly Glu Lys Pro Tyr Ala Cys Ser His Cys
        515                 520                 525

Asp Lys Thr Phe Arg Gln Lys Gln Leu Leu Asp Met His Phe Lys Arg
530                 535                 540

Tyr His Asp Pro Asn Phe Val Pro Ala Ala Phe Val Cys Ser Lys Cys
545                 550                 555                 560

Gly Lys Thr Phe Thr Arg Arg Asn Thr Met Ala Arg His Ala Asp Asn
                565                 570                 575

Cys Ala Gly Pro Asp Gly Val Glu Gly Glu Asn Gly Gly Glu Thr Lys
                580                 585                 590

Lys Ser Lys Arg Gly Arg Lys Arg Lys Met Arg Ser Lys Lys Glu Asp
        595                 600                 605

Ser Ser Asp Ser Glu Asn Ala Glu Pro Asp Leu Asp Asp Asn Glu Asp
        610                 615                 620

Glu Glu Glu Pro Ala Val Glu Ile Glu Pro Glu Pro Glu Pro Gln Pro
625                 630                 635                 640

Val Thr Pro Ala Pro Pro Ala Lys Lys Arg Arg Gly Arg Pro Pro
                645                 650                 655

Gly Arg Thr Asn Gln Pro Lys Gln Asn Gln Pro Thr Ala Ile Ile Gln
        660                 665                 670

Val Glu Asp Gln Asn Thr Gly Ala Ile Glu Asn Ile Ile Val Glu Val
            675                 680                 685

Lys Lys Glu Pro Asp Ala Glu Pro Ala Glu Gly Glu Glu Glu Glu Ala
        690                 695                 700

Gln Pro Ala Ala Thr Asp Ala Pro Asn Gly Asp Leu Thr Pro Glu Met
705                 710                 715                 720

Ile Leu Ser Met Met Asp Arg
                725

(2) INFORMATION FOR SEQ ID NO:10:

(i) SEQUENCE CHARACTERISTICS:
        (A) LENGTH: 1020 base pairs
        (B) TYPE: nucleic acid
        (C) STRANDEDNESS: double
        (D) TOPOLOGY: linear
```

(ii) MOLECULE TYPE: DNA (genomic)

(vi) ORIGINAL SOURCE:
    (A) ORGANISM: Homo sapiens (vii) IMMEDIATE SOURCE:
    (B) CLONE: c-myc (ix) FEATURE:
    (A) NAME/KEY: -
    (B) LOCATION: 531..532
    (D) OTHER INFORMATION: /label= P2
        /note= "Designates the -1 (531) and +1 (532)
        nucleotides of the P2 promoter"

(xi) SEQUENCE DESCRIPTION: SEQ ID NO:10:

```
TTCTCGTGTG GAGGGCAGCT GTTCCGCCTG GCGTAGATTT ATACTCACAG GATAAGGTAA      60
CGGTTTGTCA AACAGTACTG CTACGGAGGA GCAGCAGAGA AAGGGAGAGG GTTTGAGAGG     120
GAGCGAAAAG AAAATGGTAG GCGCGCGTAG TTAATTCAAT GCGGCTCTCT TACTCTGTTT     180
ACATCCTAGA GCTAGAGTGC TCGGCTGCCC GGCTGAGTCT CCTCCCCACC TTCCCCACCC     240
TCCCCACCCT CCCCATAAGC GCCCTCCCGG GTTCCCAAAG CAGAGGGCGT GGGGGAAAAG     300
AAAAAAGATC CTCTCTCGCT AACTCTCCGC CCACCGGCCC TTTATAATGC GAGGGTCTGG     360
ACGGCTGAGG ACCCCCGAGC TGTGCTGCTC GCGGCCGCCA CCGCCGGGCC CCGGCCGTCC     420
CTGGCTCCCC TCCTGCCTCG AGAAGGGCAG GGCTTCTCAG AGGCTTGGCG GGAAAAAGAA     480
CGGAGGGAGG GATCGCGCTG AGTATAAAAG CCGGTTTTCG GGGCTTTATC TAACTCGCTG     540
TAGTAATTCC AGCGAGAGGC AGAGGGAGCG AGCGGGCGGC CGGCTAGGGT GGAAGAGCCG     600
GGCGAGCAGA GCTGCGCTGC GGGCGTCCTG GGAAGGGAGA TCCGGAGCGA ATAGGGGGCT     660
TCGCCTCTGG CCCAGCCCTC CCGCTGATCC CCCAGCCAGC GGTCCGCAAC CCTTGCCGCA     720
TCCACGAAAC TTTGCCCATA GCAGCGGGCG GGCACTTTAC GACTGGAACT TACAACACCC     780
GAGCAAGGAC GCGACTCTCC GACGCGGGGA GGCTATTCTG CCCATTTGGG GACACTTCCC     840
CGCCGCTGCC AGGACACCGC TTCTCTGAAA GGCTCTCCTT GCAGCTGCTT AGACGCTGGA     900
TTTTTTTCGG GTAGTGGAAA ACCAGGTAAG CACCGAAGTC CACTTGCCTT TTAATTTATT     960
TTTTTATCAC TTTAATGCTG AGATGAGTCG AATGCCTAAT CTTTTCTCCC ATTCCTGCGC    1020
```

(2) INFORMATION FOR SEQ ID NO:11:

(i) SEQUENCE CHARACTERISTICS:
    (A) LENGTH: 900 base pairs
    (B) TYPE: nucleic acid
    (C) STRANDEDNESS: double
    (D) TOPOLOGY: linear (ii) MOLECULE TYPE: DNA (genomic)

(vi) ORIGINAL SOURCE:
    (A) ORGANISM: Mus musculus (vii) IMMEDIATE SOURCE:
    (B) CLONE: c-myc (ix) FEATURE:
    (A) NAME/KEY: -
    (B) LOCATION: 586..587
    (D) OTHER INFORMATION: /label= P2
        /note= "Designates the -1 (586) and +1 (587)
        nucleotides of the P2 promoter"

(xi) SEQUENCE DESCRIPTION: SEQ ID NO:11:

```
CCCGGGACGT GCGTGACGCG GTCCAGGGTA CATGGCGTAT TGTGTGGAGC GAGGCAGCTG      60
```

```
TTCCACCTGC GGTACTGATA TACGCAGGGC AAGAACACAG TTCAGCCGAG CGCTGGCGCC      120

CGAACAACCG TACAGAAAGG GAAAGGACTA GCGCGCGAGA AGAGAAAATG GTCGGGCGCG      180

CAGTTAATTC ATGCTGCGCT ATTACTGTTT ACACCCCGGA GCCGGAGTAC TGGGCTGCGG      240

GGCTGAGGCT CCTCCTCCTC TTTCCCCGGC TCCCCACTAG CCCCCTCCCG AGTTCCCAAA      300

GCAGAGGGCG GGGAAACGAG AGGAAGGAAA AAAATAGAGA GAGGTGGGGA AGGGAGAAAG      360

AGAGGTTCTC TGGCTAATCC CCGCCCACCC GCCCTTTATA TTCCGGGGGT CTGCGCGGCC      420

GAGGACCCCT GGCTGCGCTG CTCTCAGCTG CCGGGTCCGA CTCGCCTCAC TCAGCTCCCC      480

TCCTGCCTCC TGAAGGGCAG CGTTCGCCGA CGCTTGGCGG GAAAAGAAG GGAGGGGAGG       540

GATCCTGAGT CGCAGTATAA AAGAAGCTTT TCGGGCGTTT TTTTCTGACT CGCTGTAGTA      600

ATTCCAGCGA GAGACAGAGG GAGTGAGCGG ACGGTTGGAA GAGCCGTGTG TGCAGAGCCG      660

CGCTCCGGGG CGACCTAAGA AGGCAGTCT GGAGTGAGAG GGGCTTTGCC TCCGAGCCTG       720

CCCGCCCACT CTCCCCAACC CTGCGACTGA CCCAACATCA GCGGCCGCAA CCCTCGCCGC      780

CGCTGGGAAA CTTTGCCCAT TGCAGCGGGC AGACACTTCT CACTGGAACT TACAATCTGC      840

GAGCCAGGAC AGGACTCCCC AGGCTCCGGG GAGGGAATTT TTGTCTATTT GGGGACAGTG      900

(2) INFORMATION FOR SEQ ID NO:12:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:12:

GGCTTTATCT AACTCGCTGT AGTAATTCCA GCGAGA                                36

(2) INFORMATION FOR SEQ ID NO:13:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:13:

TCTCGCTGGA ATTACTACAG CGAGTTAGAT AAAGCC                                36

(2) INFORMATION FOR SEQ ID NO:14:

(i) SEQUENCE CHARACTERISTICS:
        (A) LENGTH: 483 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (vii) IMMEDIATE SOURCE:
        (B) CLONE: i1-e2

(ix) FEATURE:
        (A) NAME/KEY: -
        (B) LOCATION: 358..359
        (D) OTHER INFORMATION: /label= intron1exon2
            /note= "intron 1/exon 2 junction"
```

(xi) SEQUENCE DESCRIPTION: SEQ ID NO:14:

```
CCTCAGCCTC CCGAGNAAGC TGGGACTACA GGCGNCCACC ACCATGCCTG GCTAANTTTT        60

TTTGTATTTT TAGNAGAGGC GGGGTTTCCA CCGTGTTAGC CAGGATGTTC TCGATCTCCT       120

GACCTCGTGA TCCGCCCGCC TCAGCCTCCC AAAGTGCTGG GATTACAGGC GTGAGCCCCT       180

GCACCTGGCC AGTAGTGGTT GTTTCTTTCA TCAAGAGGCA CATGTCTGTT GTGTCTTTTT       240

TAATATTAAC AACCATTGAT GCCTAATTCA TTCACCAAAG GGTCTTTTTG TTTTAAAATG       300

TATATTTTTA TTTAGACATG CTTTGCTTTA AATAACAATC TGTGTTCTCC CTTAATAAAG       360

GCAGGGGAAA TGGAAGGTGA TGCAGTCGAA GCCATTGTGG AGGAGTCCGA AACTTTTATT       420

AAAGGAAAGG AGAGAAAGAC TTACCAGAGA CGCCGGGAAG GGGGCCAGGA AGAAGATGCC       480

TGC                                                                    483
```

(2) INFORMATION FOR SEQ ID NO:15:

(i) SEQUENCE CHARACTERISTICS:
        (A) LENGTH: 342 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (vii) IMMEDIATE SOURCE:
        (B) CLONE: E2-I2

(ix) FEATURE:
        (A) NAME/KEY: -
        (B) LOCATION: 131..132
        (D) OTHER INFORMATION: /label= exon2intron2
            /note= "exon 2 and intron 2 junction"

(xi) SEQUENCE DESCRIPTION: SEQ ID NO:15:

```
TTGACAGTGT CGATGTGTCT GTCTACGATT TCGAGGAAGA ACAGCAGGAG GGTCTGCTAT        60

CAGAGGTTAA TGCAGAGNAA AGTGGTTGGT AATATGAAGC CTCCAAAGCC AACAAAAATT       120

AAAAAGAAAG GTAAAACGAG TTTATCCATA GTGGTTTCAT AAAACCATTT TGGGATAAGC       180

ATACAACACA GTGCATATGC AAGTNGTTTT ATATTAACCG NATTTGTAAA AGGTCGTTAT       240

GTGGGTACCG CTCTTTAAAA CCAGTCTAAA ATAAGTTTTN TCCAGATTGA NTGCTCTTTT       300

NTTAATCCCA AGAAGAAGG AAATGTATTA GTGACATGAG AT                          342
```

(2) INFORMATION FOR SEQ ID NO:16:

(i) SEQUENCE CHARACTERISTICS:
        (A) LENGTH: 410 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (vii) IMMEDIATE SOURCE:
        (B) CLONE: E3-I3

(ix) FEATURE:
        (A) NAME/KEY: -
        (B) LOCATION: 20..21
        (D) OTHER INFORMATION: /label= exon3intron3
            /note= "exon 3 and intron 3"

(xi) SEQUENCE DESCRIPTION: SEQ ID NO:16:

```
ACCTTAACAC ACACACAGGT GCTGGATAAG AATGTTGGGG GCTACAACAG CAAATGCTCA      60

GACTTCGCTT TTTAGTATTC ATTCAAGCTG ACTCCAGCGG GAATTTAAAG GAAGTTTTTA     120

TTATTTCTTA TGATGCCCTT TTTGTAATCA TGATTTTATT GTAAGCACTT GGACTTAGTT     180

ATTATAGACA AATGTAAAGA AAATTTAATG AAAAATAACA CCCTCTCTCT TAAAAAAAAG     240

AAGTCTCAGG CAATAGATGC CTGGTACTAT GAGGAAGAAT GTTAGAAATA GAAGTGAAAT     300

CCCAATGAAA CCCTGTCTCT ACTAAAAATA CAAAAAATTA GCTGGGTGNG GGTGGGGGGG     360

CGCCTGTAGT CCCAGCTACT CGGGAGGCTG ATGCAGGAGA ATGGCGTGAA                410
```

(2) INFORMATION FOR SEQ ID NO:17:

(i) SEQUENCE CHARACTERISTICS:
        (A) LENGTH: 348 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: Homo sapiens (vii) IMMEDIATE SOURCE:
        (B) CLONE: I3-E4

(ix) FEATURE:
        (A) NAME/KEY: -
        (B) LOCATION: 241..242
        (D) OTHER INFORMATION: /label= intron3exon4
            /note= "intron 3/exon 4 junction"

(xi) SEQUENCE DESCRIPTION: SEQ ID NO:17:

```
CGGATTCAGA TGGGTAATTA AGAGAAACTA ATTTGGTATG TGTNATAATA TCCTGGTGTT      60

AGTATAAATT CATCCAGGCC CTCCCATAGT TTTCGGAGCT GACTTTTGTA TCTGCTTTCA     120

AGCTACTGCA GTTGATGGGA TGAATAGGGT TCCAGTCTCA TAGCAGTTCT GTGCCACACA     180

TTGAACTCTG TCATTAACTG TGCCCTTGAT CTTGCTCTTC CTGTTACTCC ATCCTTTCTC     240

TAGGTACTCG TCCTCACAAG TGCCCAGACT GCGACATGGC CTTTGTGACC AGTGGAGAAT     300

TGGTTCGGCA TCGTCGTTAC AAACACACCC ACGAGAAGCC ATTCAAGT                  348
```

(2) INFORMATION FOR SEQ ID NO:18:

(i) SEQUENCE CHARACTERISTICS:
        (A) LENGTH: 500 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: homo sapiens (vii) IMMEDIATE SOURCE:
        (B) CLONE: E4-I4

(ix) FEATURE:
        (A) NAME/KEY: -
        (B) LOCATION: 67..68
        (D) OTHER INFORMATION: /label= exon4intron4
            /note= "exon 4/inron 4 junction"

(xi) SEQUENCE DESCRIPTION: SEQ ID NO:18:

```
TCNGTNTACA ACACACCCAC GAGAAGCCAT TCAAGTGTTC CATGTGCGAT TACGCCAGTG      60
```

```
TAGAAGTGAG TGTTCAGCTT TTTGTTGGTA TCTCTCTTAG GCAGACCATG ATTTATTTCA        120

ATACAAAGCT ATAACTACTA CCCAAACGGA CTTAAGATGA GGTAGAAAAA TGTTAGTAAA        180

TTATTAACAC TCCCACACAA CACCGCTCCC CCAAAAAACT TATGATGATT GTGAAAGATT        240

TACTTGTTAA AAAGAGTCAA GTTTCTGGCT GGGTGCGGTG GCTCACGCCT ATAATCCCAG        300

CACTTTGGGA GGCTGAGGTG GCGGATCAC CTGAGGTCGG GAGTTGGAGA CCAGCTTGAC         360

AACATGGAGA AACCCGATCT TGTACTAAAA AATAAAAAAT TTAGGCTTGG GCCTGGTGGG        420

CTCACAGGCT ATNATCCCAG NAGTTTGGGG AGGCTTGAGG TGGTTTGGGA TCACAAGGTC       480

AGGAGATTGG AGACCCATCC                                                  500

(2) INFORMATION FOR SEQ ID NO:19:

(i) SEQUENCE CHARACTERISTICS:
          (A) LENGTH: 304 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: homo sapiens (vii) IMMEDIATE SOURCE:
          (B) CLONE: I4-E5

(ix) FEATURE:
          (A) NAME/KEY: -
          (B) LOCATION: 244..245
          (D) OTHER INFORMATION: /label= intron4exon5
                /note= "intron 4/exon 5 junction"

(xi) SEQUENCE DESCRIPTION: SEQ ID NO:19:

CCCTNCCCCA TAATGACCAA TCTTGGCTTA TCNATACCCG TATTCATTTA CCCACTTCTC        60

TTAGATAATG ATATGGATTC GAGAANCAAA GTTTACAAAT AATGAAGAGG GAAGAAGGTT       120

ATCTTTTAGA CTTCTGTATT CTGAACTTCA GTGCCCCAAA GCTAAGCTTT TGTGCCTAAC       180

CTACTGTGCT CTTGTTACAG TCTGTGTTAA CAGAAGTTAA AGTTCGGTTG TTTTCGTATT       240

TCAGGTCAGC AAATTAAAAC GTCACATTCG CTCTCATACT GGAGAGCGTC CGTTTCAATG       300

CATA                                                                  304

(2) INFORMATION FOR SEQ ID NO:20:

(i) SEQUENCE CHARACTERISTICS:
          (A) LENGTH: 520 base pairs
          (B) TYPE: nucleic acid
          (C) STRANDEDNESS: double
          (D) TOPOLOGY: linear (ii) MOLECULE TYPE: DNA (genomic)

(vi) ORIGINAL SOURCE:
          (A) ORGANISM: homo sapiens (vii) IMMEDIATE SOURCE:
          (B) CLONE: I5-E6

(ix) FEATURE:
          (A) NAME/KEY: -
          (B) LOCATION: 474..475
          (D) OTHER INFORMATION: /label= intron5exon6
                /note= "intron 5/exon 6 junction"

(xi) SEQUENCE DESCRIPTION: SEQ ID NO:20:

CCTCTGAATC GTTGTCAAGA NNACACATAA GGAAATAGTA CCTTTTGTNT TTGTTCCAAC        60
```

```
TTGAACCTGC CNACAACAAG NAAATTTTAA GGGAGGAATT AAGTAAAATG GACAAGATTT        120

TAATTTTAAA AGTCTGGGTA GATTTCCTAA CCTACCTTAT TCAGTTTTCC TGGATATTGT        180

CTTTTCCTAA AGAGAAAAAC TTGTGGGTTC TCCATTCAGT CTCCCCCANA GGTAAGCATT        240

GCTGTAATGT GGAGGATTCC AGAGCAGANC TGGGCAGAGC AGAGGTGGCC AGCAGCAGTT        300

TAGGACTTGG CCATATCTGA AGATAGACAA GATCCGGGAA CTGGGACTGA GCCTCAGCCT        360

TCCTAAGACC TGTAGATTCT CTGTGGTGTA GCATATCTGC CACCTGAGTT ACCCTCCAGT        420

TAAATTACAG TATTTATTCA TTTCATTTAT GTGTTCATTC TGTATTTTCT TTAAAGGGGA        480

AAAGCCTTAT GAATGTTATA TTGTCATGCT CGTTTACCCA                             520

(2) INFORMATION FOR SEQ ID NO:21:

(i) SEQUENCE CHARACTERISTICS:
        (A) LENGTH: 498 base pairs
        (B) TYPE: nucleic acid
        (C) STRANDEDNESS: double
        (D) TOPOLOGY: linear (ii) MOLECULE TYPE: DNA (genomic)

(vi) ORIGINAL SOURCE:
        (A) ORGANISM: homo sapiens (vii) IMMEDIATE SOURCE:
        (B) CLONE: E6-I6

(xi) SEQUENCE DESCRIPTION: SEQ ID NO:21:

TTATAGTGGT ACATGAAGAT GCACATTTTA CAGAAGCACA CAGAAAATGT GGCCAAATTT         60

CACTGTCCCC ACTGTGACAC AGTCATAGCC CGAAAAAGTG ATTTGGGTAA GTAGATTAAC        120

TAGTGAGAAG TGAAAAAAAT ATTTNGAAGG ATTTATATTT CGAAATATGG GGATCAAAAA        180

TAACTTCACC TTCTGACTCT CATAACATTT TATGTATAGG AATGGCCTGT CACTTAGTTT        240

AGTAAAAGCC ATTGCTTAGC TGCTTTTTTT TTTTNTNNNN NNCCTATTTC TTCCTTTNCT        300

TACTGTAGGC AGGCCACAAG ATTCTGTCCT GAGTAAAACT CATCTATAAA TTAATGGGAG        360

CTGTGATGGG AGGAGACAGA GTACACCNNT AATTAGTAGG CTCCCTTCCC CAAATAGGAA        420

AGTAACATAG TGTGATTCAA ACTCAGGTCA TCTNTTGNTT TTTTCGGGNG AACCGCCTGT        480

CCTTCCTCTA GGTAATGG                                                     498
```

ISOLATED POLYNUCLEOTIDE MOLECULES ENCODING CTCF, A CCCTC-BINDING FACTOR

RELATED APPLICATIONS

This application is a continuation-in-part of Ser. No. 08/261,680, filed Jun 17, 1994 now abandoned.

GOVERNMENT SUPPORT

This work was supported by grants TW00057 and CA20068 from the National Institutes of Health.

The U.S. government may have certain rights in the invention pursuant to a grant received from the U.S. National Institutes of Health.

BACKGROUND OF THE INVENTION

The c-myc proto-oncogene encodes a nuclear phosphoprotein with leucine zipper and helix-loop-helix structural motifs which appears to be important in the molecular biology of normal and abnormal cellular proliferation. Myc is implicated in the control of both differentiation and replication (Cole, Annu. Rev. Genet. 20:361–384 (1986)), and recent reports link myc to apoptotic cell death (Askew et al., Oncogene 6:1915–1922 (1991), Evan et al., Cell, 69:119–125 (1992), and Neiman et al., Proc. Natl. Acad. Sci. USA 88:5857–5861 (1991), each of which is incorporated herein by reference). Myc and its dimerization partner Max form stable heterodimers through their helix-loop-helix and leucine zipper domains and bind specifically to a core "E box" CACGTG DNA sequence (Blackwood et al., Science 251:1211–1217 (1991), incorporated herein by reference). Max homodimers may serve as transcriptional repressors, whereas myc/max heterodimers can activate transcription (Kretzner et al., Nature 359:426–429 (1992), incorporated herein by reference). Certain of the biological functions of myc may be mediated by transcriptional regulation of putative target genes.

Despite recent progress in defining the mechanism of myc action on "down stream" events, less progress has been made in defining the proteins regulating the expression of c-myc itself. Both transcriptional and post-transcriptional mechanisms appear to play a role in regulation of c-myc gene expression (Cole, Annu. Rev. Genet. 20:361–384 (1986), Spencer et al., Cancer Res. 56:1–48 (1991), and Marcu et al., Annual Rev. Biochem. 61:809–860 (1992), each of which is incorporated herein by reference). Maintenance of the level of the c-myc MRNA is achieved by regulation of both transcriptional initiation and elongation. Both initiation, and elongation of the c-myc mRNA, depend upon promoter elements which interact specifically with particular nuclear factors (Spencer, Oncogene 5:777–785 (1990) and Spencer et al., Cancer Res. 56:1–48 (1991), each of which is incorporated herein by reference). A general map of mouse and human c-myc transcription elements has been suggested and nuclear factors which bind to these elements have been reported. In certain cases novel cDNA's encoding such factors have been isolated and sequenced including: ZF87 (also called MAZ), a proline-rich six Zn-finger protein binding to ME1a1/ME1a2 elements within P2 promoter of the murine c-myc gene (Pyrc et al., Biochem. 31:4102–4110 (1992) and Bossone et al., Proc. Natl. Acad. Sci. USA, 89:7452–7456 (1992), each of which is incorporated herein by reference); a 37-kDa protein, MBP-1, which appears to be a negative regulator of the human c-myc promoter (Ray et al., Mol. Cell. Biol. 11:2154–2161 (1991), incorporated herein by reference); and nuclease sensitive element protein-1 (NSEP-1) which binds to a region necessary for efficient P2 initiation (Kolluri and Kinniburgh, Nucl. Acids Res. 17:4771 (1991), incorporated herein by reference). In addition, an Rb binding protein E2F which recognizes an E1A-transactivation site in the human c-myc promoter (Thalmeier et al., Genes Dev. 3:527–536 (1989), incorporated herein by reference) has also been cloned (Helin et al., Cell 70:337–350 (1992), incorporated herein by reference).

The chicken c-myc 5'-flanking region is at least 10-fold enriched in CpG-pairs compared with total chicken DNA and is presently thought to be a member of the family of CpG-rich islands involved in regulating certain house keeping genes (Bird et al., Nature 321:209–213 (1986), incorporated herein by reference). Overall high GC content (~80%) of the 5'-flanking region predicts that most of the potential regulatory DNA elements will be GC-rich. Analysis of DNA-protein interactions within the 5'-flanking region of the chicken c-myc gene revealed multiple GC-rich sequences which specifically interact with nuclear proteins (Lobanenkov et al., Eur. J. Biochem. 159:181–188 (1986), incorporated herein by reference). Proteins binding to one specific region within a hypersensitive site approximately 200 base pairs upstream of the start of transcription have reportedly been analyzed (Lobanenkov et al., Oncogene 5:1743–1753 (1990) and Lobanenkov et al., Gene Reg. and AIDS, Portfolio Publishing Corp., Texas, p. 45–68 (1989), incorporated herein by reference). Three nuclear factors were found that bind to several overlapping sequences within 180–230 bp upstream of the start of transcription. Two of the proteins appear to resemble the transcription factor Sp1, the other is a factor which seems to bind to a GC-rich sequence containing three regularly spaced repeats of the core sequence CCCTC. The CCCTC-binding factor was termed CTCF (Lobanenkov et al., Oncogene 5:1743–1753 (1990) and Lobanenkov et al., Gene Reg. and AIDS, Portfolio Publishing Corp., Texas, p. 45–68 (1989), incorporated herein by reference).

Studies suggest that during embryonic development the regulatory state of c-myc transcription can determine whether a cell continues to proliferate, or stops, and enters a pathway to terminal differentiation. Failure to properly regulate myc may be one pathway to malignancy. Thus, identifying the suppressor mechanisms by which myc is regulated would provide important reagents and assays useful in the detection of mutants that are indicative of a disease state such as cancer and the development of candidate therapeutic agents can that regulate cell proliferation, for example, inhibiting cell proliferation in cancer on the one hand, or stimulating cell proliferation in a damaged tissue on the other hand. Quite surprisingly, the present invention fulfills these and other related needs.

SUMMARY OF THE INVENTION

The present invention provides isolated and substantially pure preparations of mammalian CTCF and fragments thereof. The invention also provides antibodies to CTCF, in the form of antisera and/or monoclonal antibodies.

In another aspect the invention provides the ability to produce CTCF and polypeptides or fragments thereof by recombinant means, preferably in cultured eukaryotic cells. The expressed CTCF or fragments may or may not have the biological activity of corresponding native CTCF Accordingly, isolated and purified polynucleotides are described which code for CTCF and fragments thereof, where the polynucleotides may be in the form of DNA, such as cDNA, or RNA. Based on these sequences probes may be used to hybridize and identify these and related genes which encode CTCF. The probes may also be used to identify mutations in CTCF for diagnostic purposes. The probes may be full length cDNA or as small as from 14 to 25 nucleotides, more often though from about 40 to about 50 or more nucleotides.

In related embodiments the invention concerns DNA constructs which comprise a transcriptional promoter, a DNA sequence which encodes the CTCF or fragment, and a transcriptional terminator, each operably linked for expression of the CTCF.

In another embodiment, the polynucleotide molecules encoding CTCF and antibodies to CTCF may also be used to identify mutations in CTCF that are associated with certain diseases, such as cancer. As such the invention relates to methods for diagnosis, where the polynucleotide molecules and antibodies are used to detect the presence of CTCF mutations in a biological sample. For example, an antibody which specifically binds CTCF or a CTCF mutant is incubated with the sample under conditions conducive to immune complex formation, which complexes are then detected, typically by means of a label such as an enzyme, fluorophore, radionuclide, chemiluminescer, particle, or a second labeled antibody. Thus, means are provided for immunohistochemical staining of tissues, including tumor biopsies.

DESCRIPTION OF THE SPECIFIC EMBODIMENTS

CTCF is a sequence-specific DNA binding protein capable of binding to c-myc 5' flanking sequences. Purified CTCF has an apparent molecular weight of 130–160 kD as determined by SDS PAGE. For consistency, the molecular weight of CTCF is referred to herein as 130 kD. The present invention provides representative polynucleotide sequences encoding CTCF. As discussed in more detail herein, sequence analysis of representative CTCF cDNAs demonstrates that CTCF contains an 11-Zn-finger domain characteristic of DNA binding proteins.

The expression of the c-myc gene, which is a regulator of cell growth and differentiation, is controlled by a complex set of activation and repression controls that are mediated by a variety of transcription factors and repressors that bind to a number of elements in the c-myc flanking regions. The isolation of polynucleotide molecules encoding CTCF established that CTCF acts as a transcriptional repressor of the c-myc gene.

It is an object of the present invention to provide isolated polynucleotide molecules encoding CTCF. It is also an object of the present invention to provide methods for producing CTCF from recombinant host cells. An additional object of the present invention is to provide methods for detecting mutations in CTCF at its genetic locus that are implicated in disease states such as cancer. A feature of the present invention is an isolated polynucleotide molecule encoding CTCF. An additional feature of the present invention are antibodies directed towards CTCF that may be useful in detecting the presence of CTCF and/or CTCF mutants in biological samples such as tumor biopsies. Such isolated molecules are those that are separated from their natural environment and encompass oligonucleotides, cDNA and genomic clones. The present invention provides the advantage that CTCF encodes a protein that represses c-myc, a protein involved in the control of cell proliferation.

The present invention provides representative polynucleotide molecules and amino acids sequences encoding CTCF.

Sequences encoding CTCF include those sequences that result in minor variations in amino acid sequence, such as those due to genetic polymorphisms, differences between species and those in which blocks of amino acids have been added, altered or replaced without substantially altering the biological activity of the proteins.

Analysis of a chicken CTCF cDNA (SEQ ID NOS:4 and 5; described in more detail herein) demonstrated an open reading frame of 728 amino acids. Examination of the deduced amino acid sequence revealed 11 Zn-finger motifs (10 C2H2-type and 1 C2HC-type). CTCF could not be classified in the GLI-Kruppel class of factors (Kinzler et al., *Nature* 332: 371–374, 1988) because not all of the CTCF Zn-fingers conformed to the C2H2-type, and not all of them were consecutively connected by 6 amino acid conserved reiterated H-C links, a structural feature defining the GLI-Kruppel-like family (El-Baradi and Tomas, *Mech. Dev.* 35: 155–169, 1991; Roman et al., *New Biol.* 2: 642–647, 1990). Neither the nucleotide nor the predicted amino acid sequences outside of the Zn-finger domain showed any significant homology to genes or proteins in available databases.

As described in more detail herein, the CTCF cDNA contains domains whose functions are consistent with a DNA binding protein. Immediately C-terminal to the 11 Zn-finger domain, a glycine-rich motif is followed by a conserved lysine, which has been identified as a common nucleotide binding fold in many ATP- and GTP-binding proteins (Walker et al., *EMBO J.* 1: 945–951, 1982 and Saraste et al., *Trends in Biocem. Sci.* 15: 430–434, 1990). The presence of this putative nucleotide-binding domain in CTCF may be of functional importance. ATP and other ribonucleotide triphosphates stimulate binding of CTCF to the FpV DNA sequence. In addition, the 11 Zn-finger domain is flanked by sets of two positively charged regions with a K/R rich amino acid sequence. The most positively charged site in CTCF, a K/R rich amino acid sequence, follows the putative nucleotide-binding domain. The K/R-rich amino acid sequence is characteristic of a nuclear localization signal (NLS) (for review, see, Dingwall and Laskey, *Trend in Biocem. Sci.* 16: 478–481, 1991). The region of CTCF adjacent to the eleventh C2HC-type Zn-finger thus harbors consensus sequences for a putative ATP-binding domain, NLS and also includes potential target sites for phosphorylation by casein kinase II (CKII) and cAMP-dependent protein kinase (Pearson and Kemp, *Meth. Enzymol.* 200: 62–81, 1991). The overall arrangement (including spacing) of the eleventh C2HC-type C-terminal CTCF Zn-finger situated immediately next to the NLS followed by potential phosphorylation sites is similar to the arrangement of the C-terminal third C2HC-type Zn-finger of SWI5 (Moll et al., *Cell* 66: 743–758, 1991). Nuclear translocation of several transcription factors including SWI5 is regulated by phosphorylation of the NLS-adjacent sites (for review, see Hunter and Karin, *Cell* 70: 375–387, 1992). The similarity of arrangement of these domains between SWI5 regulatory region and CTCF indicates that nuclear import of CTCF is regulated by phosphorylation.

There are also three highly acidic domains composed of residues favorable for $\alpha$-helix formation. A helical-wheel representation of these three regions reveals a common pattern of negative residues arranged in a single "stripe" on one side of a putative helix, a feature of some strong acidic transcriptional activators (Giniger and Ptashne, *Nature* 330: 670–672, 1987).

Using poly(A)$^+$RNA from the chicken myeloid BM2 cell line and the erythroid leukemia HD3 cell line, two unequally employed start sites were mapped. Analysis of the 5' untranslated sequence of the chicken cDNA showed no apparent TATA-box upstream of either of the transcription start sites. Multiple Sp1-binding GC-rich consensus sequences (about 40) and a pyrimidine-rich initiator element (Inr) with a match to the YY1(UCRBP)-binding site (Flanagan et al., *Mol. Cell. Biol.* 12: 38–44, 1992 and Seto et al., *Nature* 354: 241–245, 1991, respectively) were present in the 5' untranslated sequence. The Inr with a YY1(UCRBP) are common features of many TATA-less promoters of house-keeping genes (for review, see, Weis and Reinberg, *FASEB J.* 6: 3300–3309, 1992). In addition, a typical E-box sequence, located between distal and proximal start sites was present, indicating that a cooperative interaction between an initiator-binding factor TFII-I and a helix-loop-helix activator may be involved in regulation of the CTCF promoter.

As described in more detail herein, three lines of evidence established that the cDNA clone encoded CTCF: (1) CTCF contained amino acid sequences corresponding to all three peptides isolated from the purified 130 kD protein; (2) when translated in vitro, the cDNA sequence encoding the 11-Zn-finger specifically bound the CTCF-binding DNA sequence recognizing exactly the same nucleotides as the 130 kD protein; (3) antibodies raised against synthetic peptides derived from the cloned sequence recognized the endogenous 130 kD nuclear protein and specifically interfered with the binding of CTCF to its DNA target in nuclear extracts. The cDNA shown in SEQ ID NO:4 was initially believed to represent one of several possible mature CTCF mRNA isoforms. However, while the CTCF cDNA depicted in SEQ ID NO:4 was believed to encode a protein of apparent 70 kD molecular weight by Western analysis (Example 6), subsequent analyses demonstrated that the CTCF cDNA encoded a protein with an apparent molecular weight between 130–160 kD (Example 10).

Analysis of a human CTCF cDNA sequence isolated from a human muscle cDNA library (SEQ ID NOS:8 and 9) showed that human CTCF shares the same structural domains as chicken CTCF: 10 Zn-fingers of the C2H2 type and one Zn-finger of the C2HC class; two highly positive domains flanking the 11-Zn-finger domain; three acidic regions in the carboxy-terminal part of the sequence and putative serine phosphorylation sites adjacent to a potential nuclear localization signal. In addition, a comparison of human and chicken CTCF amino acid sequences demonstrated that the two proteins were practically identical with an overall 96% percent similarity and 93% identity between chicken and human at the amino acid level. The amino acid sequence of the 11 Zn-finger DNA-binding domain was completely conserved.

Neither CTCF cDNA (chicken nor human) contained evolutionarily conserved sequence motifs previously found in many zinc finger proteins, such as KRAB (Witsgall et al., *Proc. Natl. Acad. Sci. USA* 91: 4513–4518, 1994 and Margolin et al., 1994); BTB (Zollman et al., *Proc. Natl. Acad. Sci. USA* 91: 10717–10721, 1994) and POZ (Bardwell et al, *Genes & Devel.* 8: 1664–1677, 1994).

While a greater than 90% homology at the amino acid level has been described for some structural DNA-binding proteins (such as histones) and for some RNA-binding proteins (such as SR proteins), it is not common among sequence specific DNA binding transcription factors. For example, even important nuclear factors p53, c-myc and c-myb have been reported to show only 47%, 70% and 82% amino acid sequence identity, respectively, between chickens and mammals (Soussi et al., *Oncogene* 5: 945–952, 1990; Watson et al., *Proc. Natl. Acad. Sci. USA* 80: 3642–36445. 1986; Query et al, *Cell* 57: 89–101, 1989).

On the nucleotide level, there was about a 20% divergence at the third DNA base pair between the human and chicken CTCF codons. In addition, while the 5'-noncoding regions of chicken and human cDNAs diverged considerably, their long 3'-untranslated regions (UTR) showed multiple domains of 100% homology that were interspersed with regions of virtually no homology indicating putative important conserved sequence that might be involved in control of CTCF mRNA turnover, cellular compartmentalization or translation efficiency. Probing at moderate stringency "Zoo"-DNA-blot with labeled representative human and chicken CTCF cDNA fragments revealed single-copy CTCF genes in frog, chicken, mouse and human genomes.

In certain instances, one may employ changes in the sequence of recombinant CTCF to substantially increase or even decrease the biological activity of CTCF, depending on the intended use of the preparation. The biological activity may be determined by measuring the binding to CTCF-target sequences in, for example, c-myc. Alternatively, biological activity may be determined by measuring cell proliferation by, for example, tritiated thymidine incorporation.

The disclosed sequences are used to identify and isolate CTCF polynucleotide molecules from suitable hosts such as canine, ovine, bovine, caprine, lagomorph, avian or the like. In particular, the nucleotide sequences encoding the 11-Zn-finger domain is used to identify poylnucleotide molecules encoding CTCF. Complementary DNA molecules encoding CTCF may be obtained by constructing a cDNA library mRNA from, for example, muscle, brain, or liver. DNA molecules encoding CTCF may be isolated from such a library using the disclosed sequences in standard hybridization techniques (e.g., Sambrook et al. ibid., and Bothwell, Yancopoulos and Alt, eds, *Methods for Cloning and Analysis of Eukaryotic Genes*, Jones and Bartlett Publishers, Boston, Mass. 1990) or by amplification of sequences using polymerase chain reaction (PCR) amplification (e.g, Loh et al. *Science* 243: 217–222, 1989; Frohman et al., *Proc. Natl. Acad. Sci. USA* 85: 8998–9002, 1988; and Erlich (ed.), *PCR Technology: Principles and Applications for DNA Amplification*, Stockton Press, 1989; and U.S. Pat. No. 4,683,195, which are incorporated by reference herein in their entirety). In a similar manner, genomic DNA encoding CTCF is obtained using probes designed from the sequences disclosed herein. Suitable probes for use in identifying CTCF sequences are obtained from CTCF-specific sequences that are highly conserved regions between human and avian CTCF coding sequences. As noted above, the sequence encoding the 11-Zn-finger domain is particularly useful for designing PCR primers. Upstream regulatory regions of CTCF are obtained using the same methods. Suitable PCR primers are between 7–50 nucleotides in length, more preferably between 15 and 25 nucleotides in length. Alternatively, CTCF polynucleotide molecules may be isolated using standard hybridization using probes of at least about 7 nucleotides in length and up to and including the full coding sequence.

The choice of hybridization conditions will generally be guided by the purpose of the hybridization, the type of hybridization (DNA—DNA or DNA-RNA), and the level of relatedness between the sequences. Methods for hybridization are well established in the literature; See, for example: Sambrook, ibid.; Hames and Higgins, eds, *Nucleic Acid Hybridization A Practical Approach*, IRL Press, Washington D.C., 1985; Berger and Kimmel, eds, *Methods in*

*Enzymology*, Vol. 52, Guide to Molecular Cloning Techniques, Academic Press Inc., New York, N.Y., 1987; and Bothwell, Yancopoulos and Alt, eds, *Methods for Cloning and Analysis of Eukaryotic Genes*, Jones and Bartlett Publishers, Boston, Mass. 1990; which are incorporated by reference herein in their entirety. The stability of nucleic acid duplexes will decrease with an increased number and location of mismatched bases; thus, the stringency of hybridization may be used to maximize or minimize the stability of such duplexes. Hybridization stringency can be altered by: adjusting the temperature of hybridization; adjusting the percentage of helix-destabilizing agents, such as formamide, in the hybridization mix; and adjusting the temperature and salt concentration of the wash solutions. In general, the stringency of hybridization is adjusted during the post-hybridization washes by varying the salt concentration and/or the temperature. Stringency of hybridization may be reduced by reducing the percentage of formamide in the hybridization solution or by decreasing the temperature of the wash solution. High stringency conditions may involve high temperature hybridization (e.g., 65–68° C. in aqueous solution containing 4–6× SSC, or 42° C. in 50% formamide) combined with washes at high temperature (e.g., 5–25° C. below the $T_m$) at a low salt concentration (e.g., 0.1× SSC). Reduced stringency conditions may involve lower hybridization temperatures (e.g., 35–42° C. in 20–50% formamide) with washes at intermediate temperature (e.g., 40–60° C.) and in a higher salt concentration (e.g., 2–6× SSC). Moderate stringency conditions may involve hybridization at a temperature between 50° C. and 55° C. and washes in 0.1× SSC, 0.1% SDS at between 50° C. and 55° C.

The invention provides isolated and purified polynucleotide molecules encoding CTCF capable of hybridizing under stringent conditions to an oligonucleotide of 15 or more contiguous nucleotides of SEQ ID NO:4 or SEQ ID NO:8 and their complementary strands. The isolated CTCF polynucleotide molecules preferably encode CTCF proteins or fragments thereof that are capable of binding c-myc regulatory regions.

The present invention provides methods for producing recombinant CTCF by inserting a DNA molecule encoding CTCF into a suitable expression vector, which is in turn used to transfect or transform a suitable host cell. Suitable expression vectors for use in carrying out the present invention will generally comprise a promoter capable of directing the transcription of a polynucleotide molecule of interest in a host cell. Representative expression vectors may include both plasmid and/or viral vector sequences. Suitable vectors include retroviral vectors, vaccinia viral vectors, CMV viral vectors, BLUESCRIPT, baculovirus vectors, and the like. Promoters capable of directing the transcription of a cloned gene or cDNA may be inducible or constitutive promoters and include viral and cellular promoters. For expression in mammalian host cells, suitable viral promoters include the immediate early cytomegalovirus promoter (Boshart et al., *Cell* 41: 521–530, 1985) and the SV40 promoter (Subramani et al., *Mol. Cell. Biol.* 1: 854–864, 1981). Suitable cellular promoters for expression of proteins in mammalian host cells include but are not limited to the mouse metallothionien-1 promoter (Palmiter et al., U.S. Pat. No. 4,579,821), and tetracycline-responsive promoter (Gossen and Bujard, *Proc. Natl. Acad. Sci. USA* 89: 5547–5551, 1992 and Pescini et al., *Biochem. Biophys. Res. Comm.* 202: 1664–1667, 1994). Also contained in the expression vectors is a transcription termination signal located downstream of the coding sequence of interest. Suitable transcription termination signals include the early or late polyadenylation signals from SV40 (Kaufman and Sharp, *Mol. Cell. Biol.* 2:1304–1319, 1982), the polyadenylation signal from the Adenovirus 5 e1B region and the human growth hormone gene terminator (DeNoto et al., *Nucleic Acid. Res.* 9: 3719–3730, 1981).

Mammalian cells may be transfected by a number of methods including calcium phosphate precipitation (Wigler et al., *Cell* 14: 725, 1978; Corsaro and Pearson, *Somatic Cell Genetics* 7: 603, 1981; Graham and Van der Eb, *Virology* 52: 456, 1973); lipofection (Felgner et al., *Proc. Natl. Acad. Sci. USA* 84: 7413–7417, 1987), microinjection and electroporation (Neumann et al., *EMBO J.* 1: 8410845, 1982). Mammalian cells can be transduced with virus such as SV40, CMV and the like. In the case of viral vectors, cloned DNA molecules may be introduced by infection of susceptible cells with viral particles. Retroviral vectors may be preferred for use in expressing CTCF in mammalian cells, particularly when CTCF is used in methods of gene therapy (for review, see, Miller et al., *Methods in Enzymology* 217: 581–599, 1994; which is incorporated herein by reference in its entirety).

It may be preferable to use a selectable marker to identify cells that contain the cloned DNA. Selectable markers are generally introduced into the cells along with the cloned DNA molecules and include genes that confer resistance to drugs, such as neomycin, hygromycin and methotrexate. Selectable markers may also complement auxotrophies in the host cell. Yet other selectable markers provide detectable signals, such as beta-galactosidase to identify cells containing the cloned DNA molecules. Selectable markers may be amplifiable. Such amplifiable selectable markers may be used to amplify the number of sequences integrated into the host genome.

As would be evident to one of ordinary skill in the art, the polynucleotide molecules of the present invention may be expressed *Saccharomyces cerevisiae*, filamentous fungi, and *E. cole*. Methods for expressing cloned genes in *Saccharomyces cerevisiae* are generally known in the art (see, "Gene Expression Technology," *Methods in Enzymology*, Vol. 185, Goeddel (ed.), Academic Press, San Diego, Calif., 1990 and "Guide to Yeast Genetics and Molecular Biology," *Methods in Enzymology*, Guthrie and Fink (eds.), Academic Press, San Diego, Calif., 1991; which are incorporated herein by reference). Filamentous fungi (e.g., strains of Aspergillus) may also be used to express the proteins of the present invention. Methods for expressing genes and cDNAs in cultured mammalian cells and in *E. cole* is discussed in detail in Sambrook et al. (*Molecular Cloning: A Laboratory Manual*, Second Edition, Cold Spring Harbor, N.Y., 1989; which is incorporated herein by reference). As would be evident to one skilled in the art, one could express the protein of the instant invention in other host cells such as avian, insect and plant cells using regulatory sequences, vectors and methods well established in the literature.

CTCF proteins produced according to the present invention are purified using a number of established methods, such as affinity chromatography using anti-CTCF antibodies coupled to a solid support and sequence-specific chromatography as described by Lobanenkov et al. (*Oncogene* 5: 1743–1753, 1990. Additional purification may be achieved using purfication means such as liquid chromatography, gradient centrifugation and gel electrophoresis among others. Methods of protein purification are known in the art (see generally, Scopes, R., *Protein Purification*, Springer-Verlag, N.Y., 1982, which is incorporated herein by reference) and can be applied to the purification of recombinant CTCF described herein.

Thus, as discussed above, the present invention provides CTCF isolated from its natural cellular environment, substantially free of other cellular proteins. Purified CTCF is also provided. Substantially pure CTCF of at least about 50% is preferred, at least about 70–80% is more preferred, and 95–99% or more homogeneity most preferred. Once purified, partially or to homogeneity, as desired, the recombinant CTCF or native CTCF may be used to generate antibodies, in assay procedures, etc.

Antisense CTCF polynucleotide molecules may be used, for example, to block expression of mutant CTCF proteins to restore normal c-myc expression. The use of antisense oligonucleotides and their applications have been reviewed in the literature (see, for example, Mol and Van der Krul, eds., *Antisense Nucleic Acids and Proteins Fundamentals and Applications*, New York, N.Y., 1992; which is incorporated by reference herein in its entirety). Suitable antisense oligonucleotides are at least 11 nucleotides in length and up to and including the upstream untranslated and associated coding sequences. The optimal length of antisense oligonucleotides is dependent on the strength of the interaction between the antisense oligonucleotides and their complementary sequence on the MRNA, the temperature and ionic environment translation in which translation takes place, the base sequence of the antisense oligonucleotide, and the presence of secondary and tertiary structure in the mRNA and/or in the antisense oligonucleotide. Suitable target sequences for antisense oligonucleotides include intron-exon junctions (to prevent proper splicing), regions in which DNA/RNA hybrids will prevent transport of mRNA from the nucleus to the cytoplasm, initiation factor binding sites, ribosome binding sites, and sites that interfere with ribosome progression. A particularly preferred target region for antisense oligonucleotides is the 5' untranslated region of the gene of interest.

Antisense oligonucleotides may be prepared by the insertion of a DNA molecule containing the target DNA sequence into a suitable expression vector such that the DNA molecule is inserted downstream of a promoter in a reverse orientation as compared to the gene itself. The expression vector may then be transduced, transformed or transfected into a suitable cell resulting in the expression of antisense oligonucleotides. Alternatively, antisense oligonucleotides may be synthesized using standard manual or automated synthesis techniques. Synthesized oligonucleotides may be introduced into suitable cells by a variety of means including electroporation, calcium phosphate precipitation and microinjection. The selection of a suitable antisense oligonucleotide administration method will generally depend on the number of cells to be treated and the type of antisense molecule used. With respect to synthesized oligonucleotides, the stability of antisense oligonucleotide-mRNA hybrids may be increased by the addition of stabilizing agents to the oligonucleotide. Stabilizing agents include intercalating agents that are covalently attached to either or both ends of the oligonucleotide. Oligonucleotides may be made resistant to nucleases by, for example, modifications to the phosphodiester backbone by the introduction of phosphotriesters, phosphonates, phosphorothioates, phosphoroselenoates, phosphoramidates or phosphorodithioates. Oligonucleotides may also be made nuclease resistant by the synthesis of the oligonucleotides with alpha-anomers of the deoxyribonucleotides.

The invention also provides synthetic peptides, recombinantly derived peptides, fusion proteins, and the like. The subject peptides have an amino acid sequence encoded by a nucleic acid which hybridizes under stringent conditions with an oligonucleotide of 15 or more contiguous nucleotides of SEQ ID NO:4 and SEQ ID NO:8. Representative amino acid sequences of the subject peptides are disclosed in SEQ ID NO:5 and SEQ ID NO:9. Particularly preferred polypeptides will include the 11 Zn-finger domain of CTCF. The subject peptides find a variety of uses including preparation of specific antibodies.

In another embodiment, the invention provides antibodies-which bind to CTCF. The production of non-human antisera or monoclonal antibodies (e.g., murine, lagomorpha, porcine, equine) be accomplished by, for example, immunizing an animal with CTCF protein or peptides with or without an adjuvant. For the production of monoclonal antibodies, antibody producing cells are obtained from immunized animals, immortalized and screened, or screened first for the production of the antibody that binds to the CTCF protein or peptides and then immortalized. It may be desirable to transfer the antigen binding regions (i.e., F(ab')2 or hypervariable regions) of non-human antibodies into the framework of a human antibody by recombinant DNA techniques to produce a substantially human molecule. Methods for producing such "humanized" molecules are generally well known and described in, for example, U.S. Pat. No. 4,816,397; which is incorporated by reference herein in its entirety. Alternatively, a human monoclonal antibody or portions thereof may be identified by first screening a human B-cell cDNA library for DNA molecules that encode antibodies that specifically bind to CTCF according to the method generally set forth by Huse et al. (*Science* 246: 1275–1281, 1989, which is incorporated by reference herein in its entirety). The DNA molecule may then be cloned and amplified to obtain sequences that encode the antibody (or binding domain) of the desired specificity.

It may be preferable to produce antibodies by genetic immunization using expression vectors to direct the expression of CTCF proteins. Particle bombardment-mediated gene transfer (Tang et al., *Nature* 356: 152–154, 1992; Eisenbaum et al., *DNA & Cell Biol.* 12: 791–797, 1993; Johnston and Tang, *Meth. Cell Biol.* 43 Pt.A:353–365, 1994; Vahlsing et al., *J. Immun. Meth.* 175: 11–22, 1994) and retroviral gene transfer (Wang et al., *DNA & Cell Biol.* 12: 799–805, 1993; Stover, *Curr. Opin. Immunol.* 6: 568–571, 1994; and Laube et al., *Human Gene Ther.* 5: 853–862, 1994) have been used to generate specific antibody responses to proteins encoded by transferred genes. These methods permit the production of antibodies without requiring protein purification. Such methods may be used to produce panels of antibodies specific to native and mutant CTCFs. Monoclonal antibodies may also be generated using-these methods. These methods find use in purification methods and methods for screening tumor biopsy samples for the presence of mutant forms of CTCF and may be useful in staging and the determination of prognosis.

Genomic localization of CTCF demonstrates that the CTCF gene locus is at 16q22. Detection of allele losses (LOH) and non-random cytogenetic abnormalities at 16q22 locus in several cancers, e.g., Wilms' tumors (Hastie, *Annu. Rev. Genet.* 28: 523–558, 1994; Huff and Saunders, *Biochim. Biophys. Acta* 1155: 295–306, 1993; and Coppes and Williams, *Cancer Invest.* 12: 57–65 1994); breast cancers (see for example, Dutrillaux et al., *Cancer Genet. Cytogenet.* 49: 203–217 1990); prostate cancer (Carter et al., *Proc. Natl. Acad. Sci. USA* 87: 8751–9755, 1990), endometrial (Fujino et al., *Cancer Res.* 54: 4294–4298, 1994) and hepatocellular (Tsuda et al., *Proc. Natl. Acad. Sci. USA* 87: 6791–6794, 1990) carcinomas, ovarian cancer (Sato et al., *Cancer Res.*

51: 5118–5121, 1991); central nervous system primitive neuroectodermal tumors (Thomas and Raffel, *Cancer Res.* 51: 639–643, 1991) and several acute myelogenous leukemias with del(16)(q22), t(3;16)(q21; q22) and t(5;16)(q33; q22) (Arthur and Bloomfield, *Blood* 61: 994–998, 1983; Betts et al., *Leukemia* 6: 1250–1256, 1992; Campbell et al., *Genes, Chromosomes & Cancer* 3: 55–61, 1991; Sanada et al., *Cancer Genet. Cytogenet.* 43: 139–141, 1989). Moreover, delineation of a minimal region of chromosome 16 long arm harboring overlapping LOH in sporadic breast tumors (Tsuda et al., *Cancer Res.* 54: 513–517, 1994; Cleton-Jansen et al., *Genes, Chrom. & Cancer* 9: 101–107, 1994), Wilms' tumors (Maw et al., *Cancer Res.* 52: 3094–3098, 1992) and hepatocellular tumors (Tsuda et al., ibid., 1990) indicates that locus 16q22 contains a tumor suppressor gene. Localization of human CTCF at 16q22 suggests that CTCF is implicated in human neoplasia.

In addition, a rare disease caused by deletion of chromosome 16 has been identified (16q- Syndrome). Fryns et al., *Hum. Genet.* 38: 343–346, 1977 and Fryns et al., *Hum. Genet.* 46: 115–120, 1979. Fujikwara et al. (*Am. J. Med. Genet.* 43: 561–564, 1992) have reported that the 16q22 locus is critical for the syndrome. Infants born with 16q-Syndrome exhibit severe growth and developmental disorders and multiple minor abnormalities.

The polynucleotide molecules, proteins and antibodies of the present invention provide methods for detecting genetic abnormalities at the 16q22 locus which has been implicated in both cancer and 16q- Syndrome. Such methods may be useful for genetic counseling, prognosis and staging of disease.

In another aspect of the invention, diagnostic methods and compositions are disclosed. Given the disclosed isolated polynucleotide molecules of the present invention and antibodies to CTCF, a variety of diagnostic assays are provided. The present invention provides a number of reagents that find use in assays to detect and/or quantitate levels of CTCF. Such reagents may be labeled with compounds that provide a detectable signal using conventional methods. Such labels include, for example, chemiluminescers, paramagnetic particles, fluorophores, radionuclides, enzymes, enzyme substrates, and the like may be used in such assay methods to facilitate detection and/or quantitation of CTCF.

Antibodies against CTCF proteins may be used as reagents to detect wild-type and/or mutant CTCF in biological samples such as tumor biopsy samples, tissue and organ sections, peripheral blood cells and the like. Within other methods, antibodies of the present invention may be used in immunoassays to detect and/or quantitate CTCF. Immunoassays suitable for use in the present invention include, but are not limited to, enzyme-linked immunosorbant assays, immunoblots, inhibition or competition reactions, sandwich assays, radioimmunoprecipitation, and the like, as generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, N.Y. (1988), each incorporated by reference herein.

In one assay format CTCF proteins are identified and/or quantified by using labeled antibodies, preferably monoclonal antibodies which are reacted with treated tissues or cells, and determining the specific binding thereto, the assay typically being performed under conditions conducive to immune complex formation. Unlabeled primary antibody can be used in combination with labels that are reactive with primary antibody to detect the CTCF protein. For example, the primary antibody may be detected indirectly by a labeled secondary antibody made to specifically detect the primary antibody. Alternatively, the anti-CTCF antibody can be directly labeled. A wide variety of labels may be employed, such as radionuclides, particles (e.g., gold, ferritin, magnetic particles, red blood cells), fluorophores, chemiluminescers, enzymes, enzyme substrates, enzyme cofactors, enzyme inhibitors, ligands (particularly haptens), etc.

DNA probes and PCR primers are designed as reagents for diagnostic assays for detecting the presence of CTCF or CTCF mutant sequences. The nature of the specific assay may depend on the type of mutational analysis to be carried out and the type of biological sample to be assayed. High molecular weight DNA may be obtained from suitable sources using commercially available kits. Commercially available kits include, the Genomic Isolation Kit A.S.A.P. (Boehringer Mannheim, Indianapolis, Ind.), Genomic DNA Isolation System (GIBCO BRL, Gaithersburg, Md.), Elu-Quik DNA Purification Kit (Schleicher & Schuell, Keene, N.H.), DNA Extraction Kit (Stratagene, La Jolla, Calif.), TurboGen Isolation Kit (Invitrogen, San Diego, Calif.), and the like. Use of these kits according to the manufacturer's instructions is generally acceptable for purification of DNA prior to practicing the methods of the present invention. PCR primers find use in the amplification of CTCF sequences from normal and diseased tissue. Such sequences may be analyzed by direct sequence analysis or by a variety of means to distinguish normal from mutant sequence. A comparison of fragment size and or comparison of sequences may be used to diagnose a number of diseases such as cancer. Within one example, CTCF-specific DNA probes are used in restriction fragment length polymorphism (RFLP) assays on DNA samples isolated from normal and diseased tissues to detect rearrangements and/or deletions of the CTCF locus. More subtle mutations may be detected by a variety of methods which include but are not restricted to single strand conformation polymorphism (SSCP) (Orita et al., *Proc. Natl. Acad. Sci. USA* 86: 2766–2770, 1989; which is incorporated by reference herein); dideoxy fingerprinting (ddf) (Orita et al., *Genomics* 5: 874–879, 1991 and Sarkar et al., *Genomics* 13: 441–443, 1992; which are incorporated by reference herein); restriction endonuclease. fingerprinting (REF) (Liu and Sommer, *BioTechnigues* 18: 470–477, 1995; which is incorporated by reference herein); PCR-based RNase protection assay (Murthy et al, *DNA & Cell Biol.* 14: 87–94, 1994; which is incorporated by reference herein) and denaturing gradient gel electrophoresis (Fodde and Losekoot, *Hum. Mutat.* 3: 83–94, 1994). These methods rely on PCR amplification of coding regions within the genes of interest and use a variety of methods to distinguish between wild-type and mutant sequences. Within other methods, exhaustive analysis of genes is carried out by sequence analysis using primer sets designed for optimal sequencing (Pignon et al, *Hum. Mutat.* 3: 126–132, 1994). The present invention provides methods by which any or all of these types of analyses may be used. As disclosed herein, a human CTCF gene and cDNA have been cloned. Using these reagents, oligonucleotide primers may be designed to permit the amplification of sequences in the CTCF gene that may then be analyzed by either direct sequencing or other indirect methods such as SSCP to identify mutations within the CTCF gene. Particularly preferred regions for designing oligonucleotide primers include intron-exon junctions. Eight exons have been mapped for human CTCF. The identification of additional exons may be obtained using standard methods such as sequencing from panels of overlapping or consecutive oligonucleotide primers and comparing the sequence to the human CTCF coding region. Intron-exon junctions are identified when the coding sequence is interrupted. Representative intron-exon junction sequences are shown in SEQ ID NOS. 14–21. Oligonucleotides for these assays are preferably designed from flanking intron sequences.

The diagnostic and screening methods of the invention find use for individuals suspected of being at risk for developing a CTCF-associated disease such as cancer or 16q22- Syndrome (e.g., family history of disease) or for patients in which such a screening is used to diagnose or eliminate CTCF-associated disease as a causative agent behind a patient's symptoms. In certain embodiments, methods for screening involve biological samples from the patient is provided (e.g., tissue biopsy and aminiotic fluid samples) and the sample is screened for the presence of mutations in CTCF. Within these methods, patient's CTCF gene is compared to normal CTCF DNA (i.e., wild-type CTCF) using a variety of methods, including RFLP analyses, SSCP, and the like, and mutations in CTCF are detected. An aberrant CTCF DNA size pattern, such as for RFLP analysis or SSCP analysis, aberrant CTCF protein and/or aberrant CTCF protein levels as determined by antibody assays would indicate that the patient has developed or is at risk to develop a CTCF-associated disease.

Prenatal diagnosis can be performed when desired, using a variety of methods to obtain fetal cells. These methods include, but are not limited to amniocentesis, chorionic villous sampling and fetoscopy. Prenatal analysis of the CTCF gene is carried out using SSCP, RFLP, DDF and the like.

Also provided are kits and multicontainer units comprising reagents and components for practicing the assay methods of the present invention. Kits of the present invention may, in addition to reagents for detecting CTCF, contain enzymatic reagents such as reverse transcriptase or polymerase; suitable buffers; nucleoside triphosphates; suitable labels for labeling the reagents for detecting CTCF and developing reagents for detecting the signal from the label. In one aspect, kits of the present invention contain sequence-specific oligonucleotide primers for detecting polynucleotide molecules encoding CTCF. Such primers may be provided in separate containers or may be provided in combinations of one or more primer pairs in a series of containers. One aspect of the invention provides kits containing CTCF sequence-specific probes. Within yet another aspect, kits contain antibodies useful for detecting CTCF in a sample. In addition to these components, the kits may also contain instructions for carrying out the assay and/or additional containers suitable for carrying out the reactions of the assay.

Within another embodiment of the invention, assays are designed for the screening of therapeutic compounds capable of replacing CTCF function or suppressing mutant CTCF function in cells containing CTCF mutants that result in abnormal cell proliferation. Within such assays, cells demonstrating abnormal cell proliferation due to a mutation in CTCF are exposed to test compounds. The cell proliferation of the treated cells are compared with the cell proliferation of untreated cells. Test compounds capable of replacing CTCF function or suppressing mutant CTCF function are those compounds that cause a reduction in the abnormal cell proliferation of the mutant cell.

In another aspect of the invention, animals, such as mice, and cell lines may be constructed that are heterozygous or homozygous for deletions of the CTCF genes. Such "knock-out" animals and cell lines may be useful as disease models and as test systems for therapeutics capable of overcoming the CTCF deletion. In one aspect of the invention, CTCF is deleted in the DT-40 cell line. This avian cell line is derived from an avian leukosis virus induced bursal lymphoma and has been demonstrated to have a high level of homologous recombination. The CTCF gene may be deleted by homologous recombination using the method essentially set forth by Buerstedde and Takeda (*Cell* 67: 179–188, 1991; which is incorporated by reference herein). In a similar manner, homologous recombination may be used to delete the CTCF gene in pluripotent mouse embryonic-derived stem (ES) cells (Thomas and Capecchi, *Cell* 51: 503–512, 1987 and Doetschman et al., *Nature* 330: 576–578, 1987; which are incorporated by reference herein). ES cells are transfected with a suitable expression vector that results in the deletion or inactivation of at least one copy of the CTCF gene in the host genome. The cells are then reintroduced into a blastocyst. Mice that develop from the injected blastocysts will generate germ-line chimeras that may then be used to produce mice that are homologous for the altered CTCF gene (for review see Capecchi, *Trends Genet*. 5: 70–76, 1989).

The following examples are offered by way of illustration, not by way of limitation.

EXAMPLE 1

Determination of Nucleotides Contacting CTCF

The region of the chicken c-myc gene protected by CTCF from cleavage generated by OP-Cu$^{2+}$ is unusually long (about 50 bp) and is shown in SEQ ID NO:1 (Lobanenkov et al., in *Gene Regulation and AIDS*: Transcriptional Activation Retroviruses and Pathogenesis, T. S. Papas (ed.), Portfolio Publishing Corp. Texas, pp 45–68, 1989; Lobanenkov et al., *Oncogene* 5: 1743–1753, 1990; Klenova et al., *Mol. Cell. Biol*. 13: 7612–7624, 1993; which are incorporated herein by reference in their entirety). This CTCF-protected region contains two Sp1-like factors and a poly (dG)-binding protein. Missing contact point analysis using all four bases was carried out according to the method set forth by Lobanenkov et al. (ibid., 1990) to determine the specific nucleotides required for CTCF binding. Briefly, 130 kD CTCF protein was purified by sequence-specific chromatography as described by Lobanenkov et al. (ibid., 1990). The purified CTCF produced only the characteristic doublet of shifted bands during EMSA (Electrophoretic mobility shift assay) on both agarose and acrylamide gels and gave exactly the same DNaseI footprint as it did in nuclear extracts. The purified CTCF protein was used in the contact point analysis to avoid contamination of CTCF-DNA complexes by other complexes containing either Sp1-like or poly(dG)-binding protein(s).

The technique of missing contact probing (Brunelle and Schleif, *Proc. Natl. Acad. Sci. USA* 84: 6673–6676, 1987; which is incorporated by reference herein in its entirety) was modified to analyze all four bases contacting CTCF. To determine all DNA bases involved in DNA recognition by the purified CTCF, missing contact analysis was carried out using either Acc I-Eco RI or Hind III-Eco RI DNA fragments of the FpV oligonucleiotide (shown in SEQ. ID. NO:2; Lobanenkov et al. (ibid., 1989)) subcloned into the pUC12. The coding sequence was end-labeled from the 3' Acc I site by reverse transcriptase and [$\alpha$-$^{32}$P]dCTP, and the non-coding strand was end-labeled at the 5' Hind III site with $^{32}$P-ATP by T4 polynucleotide kinase. Gel-purified $^{32}$P-labeled DNA fragments were modified by the C+T or G+A reactions (Maxam and Gilbert, *Methods in Enzymology* 65: 499–650, 1980), mixed with the purified CTCF protein and subjected to a preparative scale EMSA gel to separate base-modified $^{32}$P-DNA probes bound to purified CTCF protein from free DNA. Following identification of CTCF-bound bands, DNA from retarded and free bands were each isolated, cleaved by piperidine and equal amounts of radioactivity from each sample were resolved on a sequencing gel. DNA bases which on their removal/modification reduced binding by the affinity-purified CTCF protein, resulted in bands of decreased intensity in lanes displaying protein-bound DNA when compared with the free DNA. The missing contact point analysis demonstrated that 10 pyrimidines in the coding strand and 15 purines in the non-coding strand were involved in specific CTCF-DNA interaction. In addition to the CTCF-contacting nucleotides required for tight CTCF binding in the second and third direct CCCTC-repeats (Sp1-binding sites), several CG-pairs of the CGCG-GCGCG sequence (nucleotides 39 to 47 of SEQ ID NO:1) with four CpG-dinucleotides between the two Sp1-binding, were required for efficient recognition by CTCF of the entire binding region. This result may explain why several DNA sequences composed of simple repetitions of 10–12 bp-spaced CCCTC-motifs were previously found to be inefficient binding sites for CTCF (Tevosian et al., *Mol. Biol.* (Moscow) 25: 1013–1023, 1991).

To confirm the requirement for the nucleotides in the region between the two Sp1-binding sites in the 5' regulatory region of the c-myc gene, the wild-type sequence in the region between the Sp-1 binding sites was replaced with a mutant site to disrupt the CTCF binding site. The ability of CTCF to bind to the mutant sequence was then compared to the ability of CTCF to bind to the wild-type sequence. Six nucleotides of the wild-type chicken c-myc regulatory region, (cgcggc; nucleotides 39–44 of SEQ ID NO:1) were substituted with the nucleotides ATGCAT to create a new Nsi I restriction site by PCR-mediated mutagenesis. Briefly plasmid pCc-mycSA19 (Lobanenkov et al., *Eur. J. Biochem.* 159: 181–188, 1986, which is incorporated by reference herein in its entirety) containing the 598 bp Alu I-Sma I fragment of chicken c-myc (containing 5' flanking and first non-transcribed exon sequences of chicken c-myc) was subjected to polymerase chain reaction-mediated site-directed mutagenesis using the procedure described by Stappert et al. (*Nucleic Acid. Res.* 20: 624, 1992) to produce pC(Nsi)SA19. The mutation was confirmed by DNA sequence analysis. The mutant 'Nsi' DNA sequence has three CTCF-contacting CG base pairs substituted for AT pairs or for the inverse GC pair but does not alter any of the Sp1-contacting nucleotides.

To compare proteins binding to the wild-type CTCF-binding DNA region and to the 'Nsi'—mutant DNA, two 152 bp Hind III-Apa I DNA fragments (derived from plasmids pCc-myc-SA19 and pC(Nsi)SA19 plasmids, respectively) were end-labeled with α-$^{32}$P-nucleoside triphosphates (NTPs) and Klenow polymerase. The labeled DNA probes were used in modified EMSA in agarose gels with nuclear extracts from erythroid HD3 cells (Beug et al., *Cell* 18: 579–588, 1979 and Beug et al., *J. Cell. Physiol. Suppl.* 1: 195–207, 1982) essentially as described by Klenova et al. (ibid., 1993). Unlabeled 152 bp Hind III-Apa I fragments (wild-type and mutant) were used as cold competitors in these assays. A comparison of the two DNA fragments demonstrated that the Sp1-like factors and poly(dG)-binding protein were capable of binding both fragments and that no "new" protein bound the mutant DNA probe (i.e., no fortuitous protein binding site was generated by the mutation).

CTCF binding was eliminated when the 'Nsi' mutant DNA fragment was used. Furthermore, the 'Nsi' mutant DNA fragment showed an increase in the formation of complexes with poly(G)-protein and Sp1-like factors suggesting a competitive interaction between CTCF and these two factors in binding to three overlapping sequences.

In addition, competition EMSA analyses of,the CTCF DNA-binding activity using the 152 Apa II-Hind III wild-type CTCF binding DNA fragment in nuclear extracts prepared essentially as described above from cells of a number of species, from frog to human, demonstrated the conserved nature of the CTCF DNA-binding activity.

Comparative quantitative EMSA titration of DNA-binding activity of Sp1 protein and CTCF in the same nuclear extract from dividing HD3 cells demonstrated that under the moderate salt conditions two activities had practically identical binding constants and very similar concentrations suggesting that some CTCF isoforms may be as abundant as general transcription factor Sp1. Sp1 is a highly abundant ubiquitous protein (Letovsky and Dynan, *Nucleic Acid. Res.* 17: 2639–2653, 1989).

EXAMPLE 2

Effect of c-myc Mutant Promoters on CTCF Binding

To test the 'Nsi' mutation in vivo, CAT reporter gene expression vectors were constructed using either the 'Nsi' mutant c-myc promoter or the wild-type c-myc promoter. A test-reporter plasmid containing wild-type 5'-flanking non-coding sequence of the chicken c-myc gene joined to the coding sequence of the bacterial cat gene, pPst2CAT, was constructed by ligating the 3.33 kb Bam HI-Hind III DNA fragment of the pCc-mycPst2 plasmid containing 5' flanking sequences and a portion of the first non-transcribed exon of chicken c-myc (Lobanenkov et al., ibid., 1986) into Bam HI-Hind III linearized vector pKK232-8 (Pharmacia). To construct the second test-reported plasmid, the Ecl XI-Apa I fragment of the pPst2CAT was substituted for the Ecl XI-Apa I fragment containing the 'Nsi' mutant promoter sequences resulting in plasmid pPst2NsiCAT, which contained CTCF-site-mutated sequence.

HD3 cells and myeloid BM2 cells (Moscovici et al., in *Expression of Differentiated Function in Cancer Cells*, Revoltella et al. (ed.), Raven Press, New York, pp 435–449, 1982 and Symonds et al., *Mol. Cell. Biol.* 4: 2587–2593, 1984) were co-transfected by the lipofection method (Felgner et al., ibid.) with plasmids pCMV/β-gal, pRSV/Neo and either of the two test plasmids. The molar ratio of the CAT-expressing plasmid to plasmid pCMV/β-gal and plasmid pRSV/Neo was about 10:1:1, respectively. Plasmid pCMV/β-gal expresses the β-galactosidase reporter gene for normalizing transfection efficiencies. Plasmid pRSV/Neo expresses the Neo-resistance gene from an RSV LTR to facilitate selection of transfectants. As a control, the thymidine kinase gene promoter joined to the CAT gene (pTK/CAT plasmid) was co-transfected as described above and used to monitor relative "strength" of the wild-type c-myc promoter in cells of different lineage. A final control included a promoterless pKK232-8 plasmid.

Cells containing stably integrated transfected plasmids were selected in culture medium supplemented with Geneticin (G418, Gibco/BRL) at 1 mg/ml and established as separate Neo-resistant polyclonal cultures by passaging for about 5 weeks in the presence of G418. CAT-activity, normalized to the internal control β-gal activity in cell extracts prepared from an equal amount of these cells, was assayed as described (Roman et al., *New Biol.* 2: 642–647, 1990) and quantitated by a direct $^{14}$C-image analysis of the TLC plates.

Cells transfected with pPst2NsiCAT containing the 'Nsi'-mutated c-myc promoter showed a 3- and 10-fold reduction in transcription from the c-myc promoter in two different-stably transfected cell lines (HD3 and BM2 transfectants) relative to the wild-type c-myc promoter. The analysis did not distinguish between the contribution of CTCF to transcriptional regulation on the level of initiation versus the contribution of CTCF on the level of pausing and/or attenuation. However, the significance of this mutant analysis is not conclusive. Subsequent analysis of the c-myc promoter regions in the FpV DNA sequence demonstrated that an additional-binding factor Egr1 (Zif268) overlaps with the contact region required for CTCF DNA recognition. Thus the apparent transcriptional activation cannot be conclusively attributed to the action of CTCF.

EXAMPLE 3

Isolation and Characterization of cDNA Encoding 82 kD form of CTCF Protein

To obtain a cDNA encoding CTCF, partial amino acid sequence was first obtained from CTCF peptides. Briefly, CTCF was purified using sequence-specific chromatography, and the purified CTCF, which produced one polypeptide band of about 130 kD on SDS-PAGE, was cleaved with cyanogen bromide. The peptides were separated by SDS-PAGE, and the protein fragments were blotted onto polyvinyl difluoride membranes as described by Nicolas et al. ("Purification and Cloning of Transcription Factors" in *Transcription Factors: A Practical Approach*, Latchman (ed.), IRL Press, Oxford, England, pp 81–104, 1993; which is incorporated by reference herein in its entirety). The stained bands were sequenced, and three peptide sequences were obtained. Degenerate oligonucleotide probes were synthesized and used to probe Northern blots containing gel-fractionated total RNA isolated from several chicken cell lines as described by Klenova et al. (ibid.). One of the degenerate probes, corresponding to the amino acid sequence (SEQ ID NO:3) identified an RNA long enough to encode the 130 kD CTCF protein.

A cDNA library derived from poly(A)-containing RNAs of the chicken myeloid BM2 cell line (obtained from Ulrich Kruse and Albrecht E. Sippel, Institut fur Biologie III, Genetic Albert-Ludwigs Universitat, Frieburg, Germany) was probed with the degenerate oligonucleotide probe that was positive by Northern blot. One positive clone, p900, was isolated after screening approximately 7×10$^5$ phage from a library representing about 1.4×10$^6$ recombinants (Rupp et al., *Nucleic Acid. Res.* 18: 2607–2616, 1990). Sequence analysis of the p900 clone demonstrated an open reading frame (ORF) containing all three CTCF peptide sequences obtained from purified 130 kD protein. Preliminary Southern blot analysis of chicken genomic DNA indicated that CTCF was a single-copy gene locus. Two additional overlapping cDNAs, p910 and p911, were isolated by re-screening the library using the p900 cDNA as a probe. The combined sequence of the three cDNAs gave a total cDNA length of 3779 bp. To obtain the 5' end of the gene, a lambda chicken genomic DNA library (obtained from Agnes Begue and Vincent Laudet,Institut Pasteur, Lille, France) was screened with the full-length chicken CTCF cDNA, and a genomic clone was isolated. The shorter fragments of the genomic clone were subdloned and sequenced as double-stranded plasmids by the dideoxy-nucleotide chain termination method using Sequenase (United States Biochemical). One fragment overlapped the p910 cDNA, and its. sequence was joined to the 5' end of the cDNA sequence. The sequence of chicken CTCF and its deduced amino acid sequence are shown in SEQ ID NOS:4 and 5.

Primer extensions were carried out to define the putative start of transcription using several primers corresponding to the 5' end of the longest cDNA clone. Using poly(A) $^+$RNA from BM2 or HD3 cells, two unequally employed start sites were mapped: a minor distal site at designated base 221 in SEQ ID NO:4 and a major proximal site at base 552 of SEQ ID NO:4. An alignment of genomic sequence with the cDNA ORF appeared to represent authentic 5'-flanking region of the gene including 5'-end(s) of CTCF mRNAs because: (1) the transcription start sites were mapped by primer extension using different primers that hybridized within the cDNA sequence; (2) none of the several independently obtained cDNAs and none of the products of the 5'-RACE procedure had longer 5'-ends; (3) when used to probe Northern blots, genomic DNA clones representing more than 12 kb of sequence upstream of the distal start site did not detect CTCF RNA. However, the formal possibility of an additional 5' exon more than 12 kb upstream was not ruled out.

As shown in SEQ ID NO:4, the ORF consists of 728 amino acids corresponding to a polypeptide chain of 82 kD with 11 Zn-finger motifs. Analysis of the sequence showed that the first ATG codon downstream of the transcription start site was flanked by a sequence favorable for efficient translation and was preceded by two in-frame stop codons. No intron/exon junctions were discernible in the sequences between this methionine and the upstream stop codons. The three peptide sequences obtained from the purified 130 kD CTCF protein were found at amino acid positions 1–19, 229–248 and 424–438 of SEQ ID NO:5. Examination of the sequence revealed 10 C2H2-type and 1 C2HC-type Zn-finger motifs.

The 11-Zn-finger domain was flanked on each side by two positively charged regions with a K/R-rich amino acid sequence (amino acids 202–214, 255–264, 592–606 and 650–659 of SEQ ID NOS:4 and 5). A glycine-rich motif followed by a conserved lysine (amino acids 583–588 of SEQ ID NO:5), a putative nucleotide binding domain, was found in CTCF immediately C-terminal to the Zn-finger domain. The putative nucleotide-binding domain was followed by the most positively charged site in the CTCF polypeptide, a K/R-rich amino acid sequence characteristic of a nuclear localization signal (NLS). There were also three highly acidic domains (amino acids 215–235, 607–636 and 697–704 of SEQ ID NO:5) composed of residues favorable for α-helix formation. A helical-wheel representation of these three regions revealed a common pattern of negative residues arranged in a single striper on one side of a putative helix, a feature of some strong acidic transcriptional activators (Giniger and Ptashne, *Nature* 330: 670–672, 1987).

To examine CTCF expression, total cellular RNA was isolated from different chicken cell lines and from tissues by guanidinium thiocyanate extraction essentially as described by Chromczynski and Sacchi (*Anal. Biochem.* 162: 156–159, 1987; which is incorporated by reference herein). To avoid loss of resolution, 10 μg of RNA was separated on 1.5% agarose gels containing 6% formaldehyde. The RNA was blotted onto nylon membranes (Hybond N; Amersham). Plasmids p900 and p911 were used to generate random-primed DNA probes using a kit (Amersham) according to the manufacturer's instructions. The membranes were hybridized with the [α-$^{32}$P]dCTP nick-translated probes. The final blot wash was carried out in 0.1×SSPE (0.18 M NaCl, 10 mM NaPO$_4$, 1 mM EDTA (pH 7.7)) at 60° C. The Northern analysis revealed four major CTCF mRNA species indicating that CTCF gene may encode multiple proteins by generating a variety of mRNA isoforms. These included closely migrating species of about 3.7 kb and 4.0 kb and a second doublet of about 6.5 kb and 7.0 kb. Northern blots of RNA from HD3 cells, the DT40 B-cell leukemia line (Kim et al., *Mol. Cell. Biol.* 10: 3224–3231, 1990), acutely v-myc-transformed chicken embryo fibroblasts (CEF/mc29), a v-myc-transformed macrophage-like HDll cell line (Beug et al., *Cell* 18: 579–588, 1979) and in BM2 cells showed doublets of approximately 4.0 and 7.0 kb. The ratio between smaller and larger bands of the doublets varied in different cell types and was regulated by phorbol myristate acetate (PMA) and other stimuli.

EXAMPLE 4

In vitro Transcription and Translation of the 11-Zn-Finger Domain of CTCF

The DNA sequence encoding the CTCF 11-Zn finger domain was subjected to in vitro transcription and translation to determine whether the resulting protein was capable of binding to the c-myc promoter. To obtain the pCITE/CTCF1 construct for efficient in vitro translation, the CTCF Zn-finger domain was inserted downstream of the Cap-Independent Translation Enhancer (CITE) of the encephalomyocarditis virus. The Hind III-Xba I fragment of the p900 plasmid encoding all 11-Zn-fingers (amino acids 211–585 of SEQ ID NO:5) was ligated to the Nco I-Xba I linearized pCITE-1 vector (Novagen, Madison, Wis.) using Nco I-Hind III adapter. The resulting plasmid, pCITE/CTCF1 was linearized at the unique Xba I site downstream of the CTCF sequence. The linearized plasmid was transcribed with phage T7 RNA polymerase (Boehringer Mannheim Co., IN) and translated in a rabbit reticulocyte lysate system (Promega Co., Madison, Wis.) according to the manufacturers' instructions.

The in vitro translated protein was subjected to EMSA as generally described above. As expected for a smaller protein, the in vitro synthesized 11-Zn-finger domain bound to the FpV DNA fragment produced DNA/protein complexes that migrated during EMSA faster than do complexes with endogenous CTCF. Nevertheless, these complexes demonstrate competition properties listed above as diagnostic for CTCF, including the requirement for additional DNA sequence flanking contact nucleotides.

The translation product was also subjected to a methylation interference assay essentially as described by Lobanenkov et al. (ibid., 1990). The DNA probe was a 5' end-labeled at the non-coding strand of the FpV DNA fragment (described above). The guanines in the DNA fragment were partially methylated with dimethyl sulfate (DMS) by first mixing 40 μl of labeled DNA (approximately 40 ng) with 200 μl of the g$^N$ buffer (New England Nuclear). One microliter of DMS was added to the solution, and the reaction was stopped after a four minute incubation at 20° C. by the addition of 25 μl of 3 M sodium-acetate, 1 μg glycogen and 790 μl ethanol. Methylated DNA was re-precipitated twice, dissolved in 10 μl H$_2$O and used in a agarose-gel retardation assay using 1–5 μl of in vitro translation product. Following electrophoresis, the DNA was blotted onto DEAE-81 Whatman paper. The filter paper was exposed to X-ray film for 2–3 hours after which the bands of free, complex I, II and III DNA were cut out, the DNA recovered, piperidine-cleaved and analyzed on a sequencing gel.

The guanines involved in recognition of the DNA-binding domain synthesized in vitro were exactly the same as those shown to be involved in binding of endogenous 130 kD CTCF by both methylation interference assay (Lobanenkov et al., ibid., 1990), and by missing contact analysis. Thus, the in vitro translated 11-Zn-finger domain binds to the c-myc promoter DNA sequence in a manner indistinguishable from that of endogenous 130 kD CTCF protein.

EXAMPLE 5

Anti-CTCF Antibodies

Rabbit antisera against the synthetic peptides, peptide 1 (SEQ ID NO:6) and peptide 2 (SEQ ID NO:7) with C-terminal cysteines (corresponding to amino acids 2–13 and 39–50 of the CTCF sequence shown in SEQ. ID NO:5) were raised essentially as described (Lachmann et al., in *Synthetic peptides as Antigens*, Ciba Foundation Symposium 119, John Wiley & Sons, pp 25–40, 1986; which is incorporated by reference herein in its entirety) Polyclonal antibodies (operationally termed Ab1 and Ab2, respectively) were affinity-purified using Sulfo-SMCC (Pierce Chemical Co., USA) according to the protocol described by the manufacturers. The specificity of Ab1 and Ab2 for CTCF was verified by blocking experiments with the synthetic peptides used for immunizations. Preliminary characterization showed that Ab1 recognized CTCF proteins in cells of different species such as mouse NIH/3T3 cells, canine kidney MDCK cells and human fetal lung fibroblasts (HFLF); whereas Ab2 was specific for chicken CTCF as determined by indirect immunofluorescent labeling of CTCF in cells of different species using the immunoblotting method of Harlow and Lane (*Antibodies: A Laboratory Manual*, Cold Spring Harbor Laboratory, Cold Spring Harbor N.Y., 1988; which is incorporated by reference herein in its entirety) and adapted as described by Adamson et al., *J. Cell Biol.* 119: 616–627, 1992). Both Ab1 and Ab2 had identical reactivity towards CTCF proteins in chicken cells and tissues.

To determine whether the anti-peptide antibody Ab2 would specifically cross-react with endogenous CTCF, the polyclonal antisera Ab2 was subjected to EMSA analysis. The Ab2 antibody was pre-incubated in the presence and absence of its corresponding CTCF peptide and then added to a BM2 cell crude nuclear extract in the presence of 100-fold excess of poly(dI-dC), poly(dG)-poly(dC) and Sp1-binding oligonucleotides relative to the labeled 152 bp Hind III-Apa I fragment of the chicken c-myc promoter DNA probe (Example 1). Ab2 alone or Ab2 blocked by preincubation with peptide 2 was added to the binding reaction together with 2 μl of the nuclear extract thirty minutes prior to mixing with the DNA-probe mixture. The reaction was loaded onto a gel after an additional fifteen minute incubation. EMSA analysis showed that the Ab2 anti-peptide antibody specifically ablated the formation of the characteristic complexes I/II containing 130 kD endogenous CTCF.

EXAMPLE 6

Multiple Differentially Expressed forms of CTCF Protein

The anti-CTCF antibodies described above were used in Western immunoblot analysis to demonstrate the size of endogenous CTCF protein. For Western immunoblot analysis, small-scale crude nuclear preparations from chicken tissues or from cell cultures were dissolved in lysis buffer (62.5 mM Tris-HCl (pH 6.8), 1 mM $MgCl_2$ and 2.3% SDS supplemented with the proteinase inhibitor cocktail composed of 86 mg/ml PMSF, 2 mg/ml aprotinin, 40 mg/ml bestatin, 1 mg/ml leupeptin, 1.5 mg/ml pepstatin, 78.5 mg/ml benzamidine and with 1 mg/ml of DNaseI (at this concentration, DNaseI was found to degrade DNA in SDS-containing buffers)) to reduce the viscosity of samples. The samples were then mixed with an equal volume of 2× reducing SDS-gel-loading buffer and subjected to gel electrophoresis. Gel-fractionated proteins were transferred to Immobilon-P membranes (Millipore, Bedford, Mass.) by semidry blotting and probed with either Ab1 or Ab2 at a dilution of 1:100. CTCF protein bands were visualized by the Enhanced Chemiluminescence (ECL) procedure using an ECL detection system (Amersham International plc) according to manufacturer's instructions. Absence of protein degradation was confirmed by re-probing immunoblots with other antibodies (anti-tubulin or pan-anti-myc).

To study transient expression in COS-7 cells and inducible expression in stable NIH/3T3 clones, the Not I-Xba I fragment containing the full-length open reading frame of the CTCF form shown in SEQ ID NO:4 was subcloned in the pcDNA I Neo vector (Invitrogen Co., San Diego, Calif.) for high-level transient expression in COS-7 cells as described (Sambrook et al., ibid.). A second expression vector, pLK/SXneo, was made to obtain stable clones of NIH/3T3 cells conditionally expressing CTCF cDNA. In this construct, the Sma-Xba I fragment containing the same ORF was subcloned into the pLK-neo vector (Hirt et al., *Gene* 111: 199–206, 1992; which is incorporated by reference herein in its entirety) downstream of the new variant of a dexamethasone-inducible MMTV LTR. The pLK/SXneo plasmid was transfected into NIH/3T3 and several G418-resistant clones, including the NIH/3T3(C14) clone were isolated. For Western analysis, nuclear and cytoplasmic fractions of transfected cells were prepared essentially as described by Dignam et al. (*Nucleic Acid. Res.* 11: 1475–1489, 1983). When expressed in cells, it produced a nuclear protein with apparent molecular mass of 70 kD as determined by SDS-gel electrophoresis followed by Western blot analysis.

Western immunoblot analysis suggested that the CTCF gene encoded several proteins of different size that all shared an epitope recognized by the anti-CTCF polyclonal antibodies. In highly proliferating HD3 cells, two major forms were detected, two abundant 130 kD and 80 kD forms and one minor 73 kD form. The same 130 and 80 kD forms were the major CTCF proteins detected in mouse NIH/3T3(c14) cells. In dividing BM2 cells, three major forms (130, 97 and 80 kD) and two minor forms (73 and 70 kD) were present. In BM2 cells induced by PMA to terminally differentiate into macrophages (as described by Symonds et al., *Mol. Cell. Biol.* 4: 2587–2593, 1984; which is incorporated by reference herein in its entirety), the 97 kD form was down-regulated and the 73 kD form was highly up-regulated.

In preliminary experiments: (1) co-transfection experiments carried out using recipient cells which express 130 and 80 kD isoforms of the endogenous CTCF, expression of the recombinant 82 kD isoform specified by the cDNA clone SEQ ID NO:4 resulted in selective trans-repression of an indicator gene fused to the c-myc promoter and, (2) at least one domain of the 82 kD CTCF isoform (amino acids from 115 to 210 at the N-terminal side to the 11-Zn-finger domain, SEQ ID NO:5) behaved as a strong transcriptional repressor when fused to the GAL4 DNA-binding domain. These observations suggested that the major longer (130 and 80 kD) CTCF isoforms which predominate in both HD3 and BM2 cells may lack the repressor domain and/or may possess activating domain(s) absent in the cloned CTCF isoform because in these cells the CTCF-binding DNA sequence of the c-myc promoter acts as a positive transcriptional element.

Northern analysis of PMA-induced BM2-derived macrophage RNA showed no 7 kb RNA and two additional CTCF RNA isoforms (1.5 kb and 2.2 kb) suggesting that alterations in the relative proportion of different CTCF protein forms induced upon terminal differentiation of BM2 cells was due to an alteration in CTCF mRNA processing rather than to post-translational processing. CTCF protein was detected in dexamethasone-induced cells.

In lymphocytes of mature bursal follicles, a 70 kD protein accounts for almost one quarter of all CTCF proteins detected; although 80, 97 and 130 kD forms were present. The 70 kD form comigrates with the product of the chicken CTCF cDNA conditionally expressed in stably transfected NIH/3T3(c14) or transiently expressed in COS-7 cells.

None of the 97, 80, 73 and 70 kD forms were expressed in-muscle tissue of gizzard or heart, which nevertheless, produced the ubiquitous 130 kD form and a tissue-specific 55 kD form of CTCF. The smaller forms of CTCF protein were not believed to be due to in vitro proteolysis because no degradation was detected by reprobing the same blots with other antibodies; both presence and relative proportion of individual forms in different cells or tissue samples were reproducible; and pre-incubation of samples at 37° C. in the absence of proteinase inhibitors resulted in band smearing rather then in generation of additional discreet bands.

The cDNA clone shown in SEQ ID. NO:4 was believed to represent a minor mature mRNA encoding, in BM2 cells, a minor form of CTCF protein with an apparent molecular weight of 70 kD. However, subsequent analyses of human and chicken cDNAs demonstrated that the cDNAs encoded CTCF proteins of apparent molecular weight of 130 kD equivalent to the endogenous CTCF purified by sequence-specific chromatography as described in detail in Example 10.

EXAMPLE 7

Rearrangement of the Mouse CTCF Gene Locus in Friend Erythroleukemia Cell Lines

A comparison of CTCF mRNA expression from HMBA (hexamethylene bisacetamide)-induced and uninduced F-MuLV cell lines, mouse MEL cells and a human erythroleukemia cell line was carried out using Northern blot analysis. Total RNA was prepared from each of the following cell lines: HMBA-induced MEL cells including FLDS-19 (derived from F-MuLV-induced MEL clone 745A originally obtained by C. Friend (Friend et al., *Proc. Natl. Acad. Sci. USA* 68: 378–382, 1971; Ohta et al., *Proc. Natl. Acad. Sci. USA* 73: 1232–1236, 1976)); CB3 and CB7 (the CB3 and CB7 cell lines were derived from the methylcellulose colonies from spleens of BALB/c mice injected at birth with F-MuLV (Shibuya and Mak, *Proc. Natl. Acad. Sci. USA* 80: 3721–3725, 1983)); uninduced MEL cell lines FLDS-19, CB3, CB7 and human erythroleukemia cells (HEL). The RNA was resolved on a formaldehyde-agarose gel, transferred to nitrocellulose and probed with a full-length human CTCF cDNA probe. The autoradiographs demonstrated a new approximately 9 kb CTCF-containing RNA in the HMBA-induced FLDS-19 cells in addition to the approximately 5 kb CTCF message detected in all normal mouse and human cells. The 9 kb mRNA was up-regulated upon the terminal differentiation induced by HMBA suggesting that the new message was a fusion between CTCF and another HMBA-inducible gene. In addition, the CB-7 line demonstrated an 11 kb RNA that was not up-regulated with HMBA. Detection of an altered CTCF expression in the HMBA-induced FLDS-19 cells suggested that CTCF gene rearrangement(s) could be found in association with F-MuLV-induced erythroleukemia. To test this possibility, Southern analysis was carried out on high molecular weight DNA from normal and F-MuLV-transformed cell lines.

Normal and Friend erythroleukemia transformed cells lines were probed with the mouse CTCF cDNA using the Southern blot method to study the CTCF gene locus. High molecular weight DNA was obtained from the following cell lines: normal AKR1, normal NIH3T3, FLDS-19, CB3, and CB7. The high molecular weight DNA was digested with either Eco RV or Eco RI, electrophoresed through 1% agarose, transferred to nylon membranes and hybridized with a human CTCF cDNA probe. Autoradiographs of the filters demonstrated that the CTCF gene locus in some F-MuLV transformed cell lines was rearranged.

EXAMPLE 8

Transformation of Chicken Bone Marrow Cells by the Zn-finger Domain of CTCF

To investigate the role of CTCF in the control of cell proliferation and/or differentiation, a replication-competent retroviral vector encoding the 11-Zn-finger DNA-binding domain of CTCF was constructed using the PRCAS retroviral construct (Hughes et al., J. Virol. 61: 3004–3012, 1987; which is incorporated by reference herein in its entirety). The 11 Zn-finger domain of chicken CTCF was altered to insert a new Methionine codon and optimal Kozak sequence at the 5' end of the domain coding sequence and to insert an in-frame stop codon at the 3' end of the domain coding sequence using PCR-mediated methods and the pCla12-adapter intermediate (obtained from Stephen H. Hughes, Basic Research Program, Bionectics Research Inc.—National Cancer Institute Frederick Cancer Research Facility, Frederick, Md. and described by Hughes et al., ibid.). The Cla I fragment containing the newly altered 11-Zn finger domain of CTCF was inserted into the unique Cla I site in the pRCAS vector such that the insert was 3' of the splice acceptor and upstream of the LTR.

The resulting vector, designated RCAS/ZF, was transfected into primary chicken embryo fibroblasts (CEFs) to obtain virus-producing cells. The RCAS/ZF virus was collected from the transfected CEFs and used to infect bone marrow cells harvested from 7-day-old chicks. The infected cells were maintained under conditions described by Beug et al. (Cell 18: 375–390, 1979, which is incorporated by reference herein in its entirety). In 2 to 4 weeks, the cells growing out from the infected cultures were collected and passaged as a mass culture, termed BMZF1. There was no cell outgrowth from uninfected cultures or from cultures infected with a RCAS virus that did not contain CTCF coding sequences, these cultures died within one month of harvest. The BMZF1 cells were considered to be both transformed and immortalized.

The presence of the RCAS/ZF-specific 11-Zn finger domain in the immortalized BMZF1 cells was confirmed by Southern blot analysis. A diagnostic Bam HI-Bam HI 1.1 kb DNA fragment of the RCAS/ZF construct containing Zn-finger domain was detected with a CTCF probe by Southern-blot hybridization in DNA samples prepared from CEFs transfected with the pRCAS/ZF; from CEFs, infected with virus collected from transfected CEFs and from BMZF cells. Only genomic CTCF Bam HI-fragments, but no RCAS/ZF-specific 1.1 kb fragments, were detected in uninfected CEFs, in ALV-induced DT40 cells and in AMV-induced BM-2 cells. The presence of transformed, immortalized cells was indicative of the ability of the exogenously expressed 11-Zn-finger DNA-binding domain to compete with endogenous CTCF proteins. Expression of the truncated protein resulted in aberrant cell proliferation.

The BMZF1 cells were characterized by cytocentrifuging the cells onto slides and staining with hematological dyes. The cells displayed a uniform morphology characteristic of immature transformed cells of myeloid-lineage. BMZF1 cells that were treated overnight with PHA were converted to adherent macrophage-like cells with almost 100% efficiency. The conversion of these cells supports the characterization of BMZF1 cells as immature, transformed cells of myeloid lineage. In addition to the transforming activity of the RCAS/ZF virus demonstrated in vitro, when the RCAS/ZF virus was used to infect chicks, 2 out of 7 of the chickens developed tumors.

EXAMPLE 9

Human CTCF cDNA

Two primers corresponding to DNA sequences at amino acid positions 39 to 45 and 46 to 50 of SEQ ID NO:4 (which correspond to amino acids 1–6 and 7–13 of the chicken CTCF amino terminal peptide 2 (Example 5)) and three primers corresponding to amino acids 266 to 271, 276 to 282 and 283 to 288 of SEQ ID NO:4 corresponding to portions of the first CTCF Zn finger were synthesized for use as PCR primers to obtain human CTCF coding sequences.

The five primers were used in all six combinations to PCR-amplify a fragment(s) of human CTCF cDNA using the 'touchdown' PCR method described by Don et al. (Nucleic Acid. Res. 19: 4008, 1991; which is incorporated by reference herein) as modified by Roux (Biotechnigues 16: 812–814, 1994; which is incorporated by reference herein) for using nondegenerate primers. Briefly, each primer pair was used in separate reactions to amplify CTCF DNA from purified, size-fractionated, double-stranded, human muscle cDNA (Quick-clone cDNA, Clontech Laboratories, Inc.). Each reaction was heated to 93° C. for five minutes followed by a PCR regime (93° C. for one minute, annealing temperature for one minute, 74° C. for one minute for three cycles) in which the annealing temperature was lowered in two degree steps from 55° C. to 45° C. after each three cycles (per annealing temperature). The PCR regime was followed by forty cycles at the lowest annealing temperature (93° C. for thirty seconds, 45° C. for thirty seconds, 74° C. for one minute) and a final incubation at 74° C. for five minutes. The PCR reactions were carried out in an FTS-1S Capillary Fast Thermal Sequencer (A.B. Technology, Inc., Wash.). PCR products were electrophoresed in agarose gels.

One of six reactions produced discrete DNA fragments of about 600, 800 and 1100 kb. The DNA fragments were isolated and were each ligated into the TA cloning vector (Invitrogen, Calif.). Insert DNA sequences from 36 independent plasmids were determined by automated sequencing using the Tag DyeDeoxy Terminator Cycle Sequencing kit (Applied Biosystems, Inc.) according to the manufacturers instructions. A FASTA DNA sequence homology search was conducted using the Wisconsin Genetic Computing Group (GCG) package and the resulting CTCF sequences. Four of the cDNA inserts were found to have about 82% homology with the chicken CTCF cDNA sequence. One plasmid, p800-3, containing a human CTCF cDNA fragment was used to screen a Uni-ZAP XR vector (Stratagene) cDNA library prepared from poly(A)-enriched RNA of the early passage human myeloid cell line HL-60 (Collins et al., Nature 270: 347–349, 1977) by using the ZAP-cDNA synthesis kit (Stratagene, Calif.). Fourteen positive clones were helper-excised from lambda phage into the pBLUESCRIPT plasmid (Stratagene). Sequence analysis showed that the seven longest clones (inserts of approximately 3.8 kb) had identical sequences at each end. The three longest clones, p7.1, p9.1 and p10.2, were sequenced on both strands using an identical consecutive set of primers and were found to-be identical. Plasmid p7.1 has been deposited with the American Type Culture Collection Jun. 6, 1995 under Accession No. ATCC 69838 (12301 Parklawn Dr., Rockville, Md. 20852). The sequence of human CTCF and its deduced amino acid sequence are shown in SEQ ID NOS:8 and 9.

Comparison of human and chicken CTCF amino acid sequences demonstrated that the two proteins were practically identical with an overall 96% percent similarity and 93% identity between chicken and human at the amino acid level. Amino acid identity extended well outside of the completely conserved 11 Zn-finger DNA-binding domain. Analysis of the human CTCF sequence revealed the same structural domain as chicken CTCF: 10 Zn-fingers of the C2H2 type and one Zn-finger of the C2HC class; two highly positive domains flanking the 11-Zn-finger domain; three acidic regions in the carboxy-terminal part of the sequence and putative serine phosphorylation sites adjacent to a potential nuclear localization signal.

Northern blot analysis of total RNA samples from a variety of chicken, mouse and human epithelial, muscle, erythroid, myeloid and lymphoblastoid cells using the [$\alpha$-$^{32}$p]dCTP nick-translated full-length human CTCF cDNA probe under conditions essentially described by Klenova et al. (ibid, 1993) detected ubiquitous expression of an approximately 4 kb CTCF. Minor bands of about 6.5 kb which were repeatedly seen in total RNA preparations from chicken cells were absent in RNA samples from mouse and human cells. The difference between avian and mammalian Northern-blot data may indicate that unspliced CTCF mRNA precursors are more stable in avian cells.

EXAMPLE 10

In vitro Translation of a Human CTCF cDNA

As described in Examples 3 and 6, CTCF migrates as a 130 kD protein in SDS-PAGE, and the major CTCF form detected by Western immunoblotting was also about 130 kD. However, the practically identical ORF of both chicken and human approximately 3.8 kb CTCF cDNAs predicted a protein of 82 kD.

Attempts to translate the chicken CTCF cDNA in vitro using a two-step translation reaction (i.e. by in vitro CTCF mRNA synthesis in one reaction followed by in vitro translation in reticulocyte lysate in a separate reaction) were unsuccessful. This result suggested that the newly-synthesized CTCF mRNA in solution was intrinsically unstable or folded into a conformation unsuitable for translation. Given the lack of success in the two-step system, the complete sequence of the p7.1 human cDNA (Example 9) clone in plasmid pCI/CTCF and the previously described pCITE/CTCF1 template were subjected to in vitro translation using the TNT reticulocyte lysate coupled in vitro transcription-translation system (Promega Co., Madison, Wiss.) using the manufacturer's instructions. Plasmid pCI/CTCF was constructed by inserting the full-length human CTCF cDNA excised from plasmid p7.1 via flanking restriction sites into the pCI vector (Promega, Madison, Wiss.) under the CMV immediate-early enhance/promoter. Nuclear protein extracts were prepared from isolated cell nuclei by using NUN (0.3 M NaCl, 1 M urea, 1% nonionic detergent Nonidet P-40) as described by Lavery and Schibler (Genes & Dev. 7: 1871–1884 1993; which is incorporated by reference herein) and protease and phosphatase inhibitors as described previously for purification of the chicken CTCF by sequence-specific chromatography (Lobanenkov et al, ibid., 1990). The coupled T3-transcription and translation of the p7.1 CTCF cDNA clone clearly produced a single protein with about 130–160 kD mobility in SDS-PAGE. A control anti-sense T7-transcript did not translate into any protein. The difference of the apparent and predicted molecular weights expressed as a percent aberrant migration (observed-predicted)/predicted (Query et al., Cell 57: 89–101, 1989) was about 75%. The 11-Zn-finger domain of CTCF translated from the pCITE/CTCF1 plasmid, migrated in accord with its predicted size of approximately 40 kD. Thus, the amino acid sequence responsible for the aberrant migration of CTCF was probably located outside of its DNA-binding region.

Anomalous electrophoretic migration of proteins is not uncommon and has been observed with other translation products. Amino acid sequences shown to be responsible for the aberrant migration of other proteins with high (about 60%) aberrant mobility, (Query et al., ibid. and Casaregola et al., J. Mol. Biol. 228:30–40, 1992) including zinc finger proteins (Franklin et al., Mol. Cell. Biol. 14: 6773–6788, 1994). Immunoblotting carried out as described in Example 6 of in vitro translated CTCF product and endogenous CTCF loaded on the same gel demonstrated that both in vitro translated and endogenous CTCF co-migrated suggesting that the aberrant migration does not result from extensive in vivo post translational modification. In addition, EMSA assays (Example 1) using the in vitro translated product and endogenous CTCF generated EMSA retarded complexes of similar mobility.

Thus, in vitro translation demonstrated that the 727 amino acid long ORF of approximately 3.8 kb CTCF human cDNA encodes an 82 kD protein that migrates as a 130–160 kD protein in SDS-PAGE. Therefore, both chicken and human 3.8 kb cDNAs represent full-length copies of the mature CTCF polyadenylated mRNA and encode a protein identical to the endogenous CTCF.

EXAMPLE 11

CTCF Binding to Promoter-proximal Regions of c-myc Genes.

Using the in vitro translated DNA-binding domain of CTCF for gel-shift experiments, methylation interference and missing contact assays, the CTCF-binding sequences in the promoter-proximal region of mouse and human c-myc genes were determined. Four DNA fragments representing partially overlapping DNA sequences of the promoter-proximal region of both mouse c-myc (fragments $\alpha$, $\beta$, $\gamma$, and $\Delta$) and human c-myc (fragments A, B, C and $\Delta$) genes were synthesized by PCR-amplification with pairs of 15–22 bp primers (one of each pair was 5'-end-labeled with [$\gamma$-$^{32}$P] ATP and T4-kinase) in order to obtain DNA-probes suitable for both EMSA assay and methylation interference experiments. The resulting probes were: A (from −56 to +111 relative to +1 at the P2 initiation site, corresponding to nucleotides 476–652 of SEQ ID NO:10), B (from −225 to −38 relative to +1 at the P2 initiation site; corresponding to nucleotides 307 to 494 of SEQ ID NO:10), C (from −353 to −166 relative to +1 at the P2 initiation site; corresponding to nucleotides 179–366 of SEQ ID NO:10), D (from −489 to −329 relative to +1 at the P2 initiation site; corresponding to nucleotides 43 to 203 of SEQ ID NO:10), α (from −237 to −87 relative to +1 at the P2 initiation site; corresponding to nucleotides 350 to 500 of SEQ ID NO:11), β (from −157 to +18 relative to +1 at the P2 initiation site; corresponding to nucleotides 430 to 604 of SEQ ID NO:11), γ (from −49 to +113 relative to +1 at the P2 initiation site; corresponding to nucleotides 538 to 699 of SEQ ID NO:11) and Δ (from +85 to +254 relative to +1 at the P2 initiation site; corresponding to nucleotides 671 to 840 of SEQ ID NO:11) of the mouse c-myc. As a positive control for CTCF binding, a DNA fragment covering the FpV region of the chicken c-myc promoter (SEQ ID NO.:2) was amplified from plasmid pFpV (Lobanenkov et al., ibid., 1989). These fragments were gel-purified using Elutip-D (Schleicher and Schuell) mini-column chromatography and utilized for both EMSA and methylation interference and missing contact analyses.

EMSA reactions were carried out for each DNA probe with 1 μl to 10 μl of the in vitro translation product (Example 10) or nuclear extract (Example 1) in the presence of cold double-stranded competitor DNAs [poly(dI-dC), plus poly (dG)-poly(dC), plus oligonucleotide containing strong binding sites for both Sp1 and Egr1 proteins] in the "PBS-based" buffer (standard phosphate buffered saline with 5 znZ NgCl$_2$, 0.1 mM ZnSO$_4$, 1 mM DTT, 0.1% Nonidet P-40 and 10% glycerol). Reactions were incubated for 30 minutes at room temperature and then analyzed on 5% polyacrylamide gels run in 0.5× TBE buffer. Results of the EMSA demonstrated that in addition to the control FpV, three out of eight DNA fragments efficiently bound CTCF protein (fragments A and B from the human c-myc gene and fragment γ from the mouse gene). A comparison of the proportions of each DNA probe bound by an equal amount of CTCF indicated that the binding affinity of CTCF to fragments A, B and γ was comparable to that for chicken FpV. Binding to fragment C was weaker and was not characterized further. Cold DNA fragments A, V and Δ were used as competitors in a cross-competition EMSA experiments. The cross-competition EMSA demonstrated that Fragment A efficiently competed for CTCF binding to itself and to fragments FpV and B; fragment FpV competed for binding to itself and to fragments A and B; whereas fragment D which did not bind CTCF, did not compete for CTCF binding.

To determine exactly which nucleotides were recognized by CTCF in human and mouse fragments A, B and γ, and to compare them with the recognition sequence in the chicken FpV, missing contact analysis (for C plus T bases) and methylation interference (for G bases) assays were carried out on both strands of each DNA fragment essentially as described in Examples 1 and 4 (and described in detail by Lobanenkov et al., ibid., 1989, Lobanenkov et al., ibid., 1990; and Klenova et al., ibid., 1993). Briefly, each of four DNA fragments (A, B, γ, and FpV) was 5'-end-labeled at either the top (coding) strand or at the bottom (anti-coding) strand, then either partially methylated at guanines with dimethyl sulfate or modified at pyrimidine bases with hydrazine by the C+T reaction of Maxam and Gilbert (ibid.) and incubated with the in vitro translated DNA-binding domain of CTCF (Example 10). Free DNA probe was separated from the CTCF-bound probe by preparative EMSA, DNA isolated from the gel, cleaved at modified bases with piperidine, and analyzed on a sequencing gel as described in detail previously (Lobanenkov et al., ibid., 1990; Klenova et al., ibid., 1993 and detailed in Example 1). DNA bases which on their removal/modification reduced binding by the affinity-purified CTCF protein, resulted in bands of decreased intensity in lanes displaying protein-bound DNA when compared with the free DNA.

Inspection of bases required for CTCF binding to four DNA sequences revealed that: (1) in fragments A and γ, CTCF bound a DNA sequence +5 to +45 position downstream of the P2 initiation site of both human and mouse c-myc promoters; (2) in fragment B, CTCF bound a GC-rich sequence immediately downstream to the P1 initiation site; (3) the P2-proximal CTCF-binding sequence was well conserved in the two mammalian c-myc genes; moreover, five nucleotides that were different within this site in mouse and human sequences were not involved in contacting CTCF; and (4) the P2-proximal conserved CTCF-binding sequence of human and mouse c-myc genes was different from the P1-proximal CTCF-binding sequence of the human gene and also from the CTCF-binding sequence FpV in the chicken c-myc gene.

A comparison of four DNA sequences positive for CTCF binding with several sequences negative for CTCF strongly suggested that the CCCTC-like motif formerly implicated in CTCF-DNA recognition, may be necessary but certainly is not sufficient for tight binding. In order to prove this point, three CTCF-contacting bases unique for the P2-proximal CTCF-binding site and located far away from the GC-rich core common for all 4 CTCF-binding sites was mutated. Briefly, a wild-type c-myc-CAT reporter expression vector, pAPwtCAT, was constructed by ligating the Apa I-Pvu II fragment of the human c-myc 5' noncoding region from position −121 to +352 relative to the P2 site from a plasmid containing the entire c-myc gene into pBLCAT3, a promoterless CAT construct (Luckow and Schutz, *Nucleic Acid. Res.* 15: 5490, 1987; ATCC 37528).

The mutant c-myc promoter was obtained by replacing the nucleotide sequence TGT at positions +8 to +10 relative to the P2 initiation site (nucleotides 539–541 of SEQ ID NO:10) with ACA by two step amplification (Kammann et al., *Nucleic Acid. Res.* 17: 5404, 1989; Herlitze and Koenen, *Gene* 91: 143–147, 1990; Perrin and Gilliland, *Nucleic Acid. Res.* 18: 7433–7438, 1990; Landt et al., *Gene* 96: 125–128, 1992; and Marini et al., *Nucleic Acid. Res.* 21: 2277–2278, 1993; which are incorporated by reference herein) using two mutant primers and two flanking wild-type primers. A sense primer, A, representing nucleotides 347–366 of SEQ ID NO:10, an antisense primer, B, corresponding to nucleotides 708–732 of SEQ ID NO:10, a sense mutagenic primer (SEQ ID NO:12) and an antisense mutagenic primer (SEQ ID NO:13) were synthesized for the mutagenesis reactions. A plasmid containing the human c-myc gene as the template. In one reaction the template plasmid was mixed with the sense primer, A, and the antisense mutagenic primer (SEQ ID NO:13). In the other reaction, the template plasmid was mixed with the antisense mutagenic primer B and the sense mutagenic primer (SEQ ID NO:12). The reaction mixtures were incubated at 93° C. for five minutes followed by 40 amplification cycles of (93° C. for 1 minute, 55° C. for 1 minute, 74° C. for 1 minute). The PCR reactions were placed at 4° C. until the second PCR reaction was carried out. The PCR products from the first reaction were separated from the primers, and the purified products were pooled. The pooled reaction products were subjected to amplification with sense primer A and antisense primer B using the conditions set forth above. The reaction product from the second amplification was purified by agarose gel electrophoresis and digested with restriction enzymes that cut at unique sites flanking the mutated site. The fragment was used to replace the analogous fragment in pAPwtCAT to construct pAPacaCAT. The mutant sequence was verified by sequencing.

EMSA (Example 1) using the in vitro translated DNA-binding domain demonstrated that the mutation knocked out CTCF binding. Therefore, contact bases critical for recognition by CTCF could clearly be different in a number of different were clearly different in two different CTCF-binding sequences found in the chicken FpV and in the human fragment A.

DNA base recognition code employed by multifinger factors has been defined by three amino acids at the tip of an individual Zn finger (Desjarlais and Berg, *Proc. Natl. Acad. Sci. USA* 89: 7345–7349, 1992), this indicated that CTCF should employ different combinations of Zn-fingers in order to contact different arrangements of DNA bases. To demonstrate whether deletion of particular fingers will maintain binding to a particular CTCF recognition DNA sequence but result in a loss of specific binding to another recognition sequence, in vitro translated forms of CTCF DNA-binding domains were prepared in which Zn-finger domains were successively truncated from each protein terminus. The in vitro translated products of the truncated CTCF binding domain were used in EMSA analysis with DNA fragments FpV and A. EMSA analysis showed that N-terminal fingers 1 and 2 were dispensable for binding to the P2-site, but required for binding to the FpV sequence. On the other hand, C-terminal fingers 8, 9, 10 and 11 were absolutely required for binding to the P2-proximal site of the human c-myc but dispensable for binding to the site V of the chicken c-myc. Given this ability to recognize and bind to different DNA sequences by employing different groups of Zn-fingers, CTCF is a "multivalent" factor.

Taken together, the strict evolutionary conservation of CTCF and its ability to bind specifically to a number of different DNA sequences in the promoter-proximal regions of human, mouse and chicken c-myc genes suggests that it may play a very important role in regulation of c-myc genes in vertebrate species.

EXAMPLE 12

Repression of the Human c-myc P2-promoter by CTCF

As noted above, one of two high-affinity CTCF-binding sites in the human c-myc promoter consists of nucleotides from +5 to +45 relative to the P2 initiation site. This sequence coincides with the +30 position of the polymerase II transcription pausing and promoter melting (Krumm et al., *Genes & Devel.* 6: 2201–2213, 1992). Modulation of the P2-proximal transcription pausing at this site was shown to be a major regulatory mechanism of the human c-myc expression during cell growth and differentiation (for review see Spencer et al., *Genes & Devel.* 4: 75–88, 1990 and Spencer and Groudine, *Adv. Cancer Res.* 56: 1–48, 1991). To analyze the functional contribution of both endogenous and exogenous CTCF binding to the P2-proximal site of the human c-myc gene, plasmids pAPwtCAT and pAPacaCAT were compared in vivo.

The vectors were transfected essentially as described in Example 2, and polyclonal stably transfected cell lines were established by pooling all G418-resistant clones from each transfection. In stable transfection experiments, CAT activity, normalized to the internal copy number control β-galactosidase activity, was assayed in cell extracts prepared from an equal number of transfected cells as described (Seed and Sheen, *Gene* 67: 271–277, 1988). Since transcription of the endogenous c-myc gene is dependant on cell growth conditions (for review see Marcu et al., *Ann. Rev. Biochem.* 61: 809–60, 1992), the contribution of CTCF to the regulation of the promoter activity might also be dependant on the proliferation status of stably transfected cells. Therefore, CAT activity was measured in cells grown under three different conditions: (1) normal growth, when cells were passaged every third day and did not reach confluence; (2) growth arrest, when confluent cells were kept in serum deprived media for 2.5 days; (3) serum response, when confluent cells were serum-starved for 2 days and then transferred to a fresh serum containing media for 12 hours prior to harvest. Under all three different cell growth conditions, pAPacaCAT transfectants (the "ACA" mutation in PAPacaCAT eliminated CTCF binding to the +30 site of the P2 promoter) had 3- to 6-fold increase reporter gene transcription activity suggesting that CTCF binding inhibits P2 promoter activity. The repressing effect of CTCF binding to the P2-proximal site (the wild-type c-myc promoter in pAPwtCAT) appeared most profound in growth-arrested cells (i.e. under conditions when transcription from the c-myc promoter was reported to be inhibited (Kelly and Siebenlist, *Ann. Rev. Immunol.* 4: 317–338, 1986)). Thus, mutational analysis of the P2-proximal CTCF-binding site strongly suggested that CTCF is a repressor of transcription from the major human c-myc gene promoter.

To examine the ability of exogenously supplied CTCF to repress the c-myc P2 promoter transient co-transfection experiments were performed in human embryonic kidney 293 cells by using the pHIV-LTR/β-gal for normalizing transfection efficiency; the pCI/CTCF expression vector as an effector, and pAPwtCAT and pAPacaCAT as reporter constructs. A number of co-transfection experiments and EMSA assays were initially carried out to ensure that: (1) in 293 cells, the pCI/CTCF expression vector was able to produce CTCF, detectable by Western immunobloting, at levels proportional to the amount of transfected plasmid; (2) transient transfection into 293 cell line reproducibly resulted in sufficient signal from the CAT-constructs containing only the P2-proximal c-myc promoter region; and (3) the HIV LTR-driven β-gal construct employed as an internal control for cell transfection efficiency, neither itself binds to nor responds to CTCF. CAT activity, normalized to the internal copy number control β-gal activity, was assayed in cell extracts prepared from equal number of transfected cells as described (Seed and Sheen, ibid., 1988).

The transient co-transfection experiments were potentially complicated by endogenous CTCF present in target cells which might repress reporter constructs and mask any effect of the exogenous CTCF. Therefore, to assess any effect of exogenous CTCF produced by the transfected expression vector, conditions were established in which endogenous CTCF was limiting with respect to the transfected target constructs (i.e. binding of endogenous CTCF was saturated). Under such conditions an excess of target constructs free of bound endogenous CTCF should respond to exogenous CTCF produced by the co-transfected expression vector. The results of the experiments demonstrated that with an input of 1 μg of c-myc-promoter/CAT constructs per transfection, the target constructs appeared to be in "excess" since there was little difference in CAT reporter activity between the wild type and mutated constructs. Under these conditions introducing as little as 0.2 μg of CTCF-expression vector resulted in the repression of the wild type but not the "ACA"-mutated promoter indicating that the sequence-specific interaction of exogenously expressed CTCF with the P2-proximal DNA region can specifically repress the promoter. At higher input of exogenous CTCF (2.0 μg and 10 μg of expression vector), a stronger repression was achieved. However some of this stronger repressing effect did not require binding of CTCF to the P2-proximal site because the ACA-mutated promoter also became repressed. This finding indicated that at high input level CTCF can either bind to additional low-affinity sites in the promoter or interact with other transcription factors involved in transcription from the P2 promoter of the human c-myc gene. since in cotransfection experiments with several other promoters, including HIV LTR, MuLV LTR, SV40 and HSV TK showed no promoter suppression even at high levels of exogenously expressed CTCF indicating that the interaction may be quite specific for the P2 c-myc promoter. Taken together, data of mutational analysis and co-transfection experiments showed that CTCF is a repressor of the human c-myc P2 promoter.

EXAMPLE 13

Chromosomal Location of the Human CTCF Gene

A human fibroblast genomic library in the lambda FIXII vector (Stratagene, Calif.) was screened with either fragments or full-length human CTCF cDNA. DNA from positive lambda clones were partially mapped with several restriction enzymes and sequenced by using multiple primers corresponding to different regions of the cDNA sequence. One positive clone was identified that contained an approximately 18 kb insert. Purified DNA from the bacteriophage clone was labeled with digoxigenin-dUTP (Boehringer Mannheim) by nick translation according to the manufacturers instructions and used for immunofluorescent in situ hybridization (FISH) with normal metaphase chromosome derived from PHA-stimulated peripheral blood lymphocytes. A total of 75 metaphase cells were analyzed with 56 exhibiting specific labeling. FISH analysis showed that the human CTCF gene is located on the long arm of chromosome 16. Measurements of 10 specifically labeled chromosomes with both CTCF probe and the centromere-specific chromosome 16 probe (BIOS Labs, Inc.) showed that CTCF is located 61% of the distance from the centromere to the telomere of the chromosome arm 16q, an area that corresponds to the band 16q22.

EXAMPLE 14

Rearrangement of the CTCF Gene Locus in Certain Breast Cancers

Restriction fragment length polymorphism (RFLP) analysis of CTCF genomic locus was carried out in eleven breast cancer cell lines to determine whether rearrangements had occurred at the CTCF locus. The eleven breast cancer cell lines ZR-75-1, MCF7, BT-474, BT-483, BT-549, MDA-MB-231, SK-BR-3, Hs 578T, MDA-MB-435S, MDA-MD-453, and T-47D were obtained from the American Type Tissue Collection (Rockville, Md.) or kindly provided by V. Seewaldt and Karen L. Swisshelm (Department of Pathology, University of Washington, Seattle). DNA from these cell lines was prepared with the DNA isolation kit (Qiagen, Chatsworth, Calif.) according to manufacturers' instructions. Normal human DNA was used as a control. RFLP analysis was carried out using restriction digestion of genomic DNA with Eco RI followed by agarose gel electrophoresis. Eco RI was used because it did not show any polymorphisms in more than 50 DNA samples representing different individuals. Southern blots were prepared and probed with the human CTCF cDNA probe labeled with [$\alpha$-$^{32}$P]dCTP by nick-translation. The blots were washed in 0.1× SSC at 65° C. (Sambrook at el., ibid. 1989). Of the eleven cell lines screened, in two breast cancer cell lines, BT474 and T47D, the Eco RI map of CTCF gene was altered and in one cell line, BT474, the second CTCF allele was certainly lost because one Eco RI fragment was missing. The other cell lines displayed identical normal Eco RI bands.

Blood and tumor DNA samples were obtained from four breast cancer patients, with the approval of the local ethics committee, from a clinic of oncology in Stockholm, Sweden. Tumors used in this study were removed surgically prior to radiation or chemotherapy and characterized as described (Lindblom et al., *Cancer Res.* 53: 3707–3711, 1993). High molecular weight DNA from peripheral leukocytes and tumor tissue was isolated as described (Larsson et al., *Genes Chromosomes Cancer* 2: 191–197, 1990). RFLP analysis using Eco RI was carried out and the autoradiographs showed that one patient sample had rearrangement of the CTCF locus.

All publications and patents mentioned in this specification are herein incorporated by reference into the specification to the same extent as if each individual publication or patent was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. An isolated and purified nucleic acid molecule which hybridizes under stringent conditions comprising hybridization at 65–68° C. in aqueous solution containing 4–6× SSC, or 42° C. in 50% formamide to a polynucleotide molecule which codes for a CCCTC-binding factor (CTCF) polypeptide, or the full length complement of said polynucleotide molecule, wherein the CTCF polypeptide comprises the contiguous amino acid sequence of SEQ ID NO: 5 or a fragment thereof, which CTCF polypeptide or fragment thereof binds a c-myc 5'-flanking sequence.

2. The nucleic acid molecule of claim 1, which is a genomic DNA sequence, a cDNA sequence, or an RNA antisense sequence.

3. The nucleic acid molecule of claim 1, which codes for human CTCF polypeptide as depicted in SEQ ID NO: 9.

4. The nucleic acid molecule of claim 1, which hybridizes under stringent conditions comprising hybridization at 65–68° C. in aqueous solution containing 4–6× SSC, or 42° C. in 50% formamide to an oligonucleotide of 25 or more contiguous nucleotides of SEQ ID NO: 4 or SEQ ID NO:8, or the full length complement of said oligonucleotide and which codes for a polypeptide which binds to a c-myc 5'-flanking sequence or a 11-Zn-finger binding domain thereof.

5. An isolated and purified nucleic acid molecule which encodes a CTCF polypeptide as depicted in SEQ ID NO: 5 or SEQ ID NO: 9.

6. A DNA construct comprising the following operably linked elements:

a transcriptional promoter;
   a DNA sequence which hybridizes under stringent conditions comprising hybridization at 65–68° C. in aqueous solution containing 4–6× SSC, or 42° C. in 50% formamide to a polynucleotide molecule encoding a CTCF polypeptide or the full length complement of said polynucleotide molecule, wherein the CTCF polypeptide comprises the contiguous amino acid sequence of SEQ ID NO: 5 or a fragment thereof, which CTCF polypeptide or fragment thereof binds a c-myc 5'-flanking sequence; and
   a transcriptional terminator.

7. The DNA construct of claim 6, wherein the DNA sequence encodes the human CTCF polypeptide of SEQ ID NO: 9.

8. The DNA construct of claim 6, wherein the DNA sequence encoding the CTCF polypeptide is the sequence set forth as SEQ ID NO: 4 or SEQ ID NO: 8.

9. A cultured prokaryotic or eukaryotic cell transformed or transfected with a DNA construct which comprises the following operably linked elements:

a transcriptional promoter;

a a DNA sequence encoding the CTCF polypeptide as depicted in SEQ ID NO: 5 or SEQ ID NO: 9 or a fragment thereof which binds to a c-myc 5'-flanking sequence; and a transcriptional terminator.

10. The eukaryotic cell of claim 9, which is a mammalian cell.

11. The eukaryotic cell of claim 9, wherein the DNA sequence encodes the human CTCF polypeptide as depicted in SEQ ID NO: 9.

12. The eukaryotic cell of claim 9, wherein the DNA sequence encoding the CTCF polypeptide is the sequence set forth as SEQ ID NO: 4 or SEQ ID NO: 8.

13. The prokaryotic cell of claim 9, which is an *E. coli* cell.

14. A method for producing a CTCF polypeptide, which comprises:

growing eukaryotic cells transformed or transfected with a DNA construct which comprises the DNA construct of claim 8 which expresses CTCF, and isolating the CTCF polypeptide from the cells.

15. The method of claim 14, wherein the cells are cultured mammalian cells.

16. The method of claim 14, wherein the DNA sequence expresses human CTCF polypeptide as depicted in SEQ ID NO: 8.

* * * * *